United States Patent [19]
Poretz et al.

[11] Patent Number: 5,935,790
[45] Date of Patent: Aug. 10, 1999

[54] METHOD FOR DETECTING A PREDISPOSITION TO SUSCEPTIBILITY TO TOXIC EFFECTS OF DRUGS AND POISONS

[75] Inventors: Ronald D. Poretz, Marlboro; Paul Manowitz, East Brunswick, both of N.J.

[73] Assignees: Rutgers, The State University of New Jersey; University of Medicine and Dentistry of New Jersey, both of Piscataway, N.J.

[21] Appl. No.: 08/910,443

[22] Filed: Aug. 5, 1997

Related U.S. Application Data

[60] Provisional application No. 60/022,493, Aug. 6, 1996.

[51] Int. Cl.$^6$ ....................................................... C12Q 1/68
[52] U.S. Cl. ............................................. 435/6; 536/24.31
[58] Field of Search ............................... 435/6; 536/24.31

[56] References Cited

U.S. PATENT DOCUMENTS

| | | |
|---|---|---|
| 4,946,778 | 8/1990 | Ladner et al. . |
| 5,639,607 | 6/1997 | Desnick et al. . |

FOREIGN PATENT DOCUMENTS

| | | |
|---|---|---|
| WO 92/08981 | 5/1992 | WIPO . |
| WO 93/03185 | 2/1993 | WIPO . |
| WO 93/03367 | 2/1993 | WIPO . |
| WO 96/07098 | 3/1996 | WIPO . |
| WO 96/18336 | 6/1996 | WIPO . |

OTHER PUBLICATIONS

Barth et al(1994) J Med Genet 31:667–71.
Baum et al(1959) Clin Chem Acta 4:453–5.
Brun and Brun(1974) Acta Pathol Microbiol Scand 82:311–8.
Chabas et al(1993) Clin Genet 44:320–23.
Conzelmann and Sandhoff(1983) Dev Neurosci 6:58–71.
Cory–Slechta(1995) Neurotoxicology 16:83–96.
Fressinaud et al(1989) J Cell Physiol 141:667–74.
Furst and Sandhoff(1992) Biochem Biophys Acta 1126:1–16.
Gieselmann et al(1991) Hum Genet 86:251–5.
Gieselmann et al(1989) Proc Natl Acad Sci USA 86:9436–40.
Gorman and Poretz(1987) J Cell Physiol 131:158–164.
Hohenschutz et al(1989)Hum Genet 82:45–8.
Hohenschutz et al(1988) Am J Med Genet 31:169–75.
Huse et al(1989) Science 246:1275–81.
Kappler et al(1991) Hum Genet 86:463–470.
Kodoh and Wenger(1982) J Clin Invest 70:89–97.
Lee and Poretz(1991) Immunol Cell Biol 69:151–7.
Leinekugel et al(1992) Hum Genet 88:513–23.
Lemons and Theone(1991) J Biol Chem 266:14378–82.
Lowry et al(1951) J Biol Chem 193:262–75.
Manowitz et al(1981) Biol Phychiat 16:1107–13.
Markowitz and Rosen(1991) J Pediatr 119:305–10.
Naidu(1995) In: The MRI Suggests a Leukodystrophy, But Tests Are Negative. What Should We Do? Tager ed. United Leukoduatrophy Foundation, Inc: Sycamore, IL, p. 38.
Needleman(1993) Neurotoxicology 322:83–8.
Nelson et al(1991) Hum Genet 87:87–8.
Neskovic et al(1986) J Neurochem 47:1412–8.
Orsi et al(1987) Adv Aerobiol 51:243–8.
Park et al(1996) Alcoh: Clin Exp Res 20:234–9.
Penzien et al(1993) Am J Med Genet52:557–64.
Proretz et al(1992) Biochem J 287:979–83.
Richards et al(1993) Hum Molec Genet 2:159–63.
Ricketts et al (1996) J. Effective Disorder 40:137–47.
Ricketts et al(1995) Neuropsych Genet.
Rosen(1995) Toxicology 97:11–7.
Santra et al(1989) Ind J Biochem Biophy 26:92–7.
Shen et al(1993) Am J Med Genet 45:631–7.
Stein et al(1989) J Biol Chem 264:1252–9.
Tiffany–Castiglioni et al(1986) Toxicology 42:303–15.
Van der Pal et al(1990) Biochem Biophys Acta 1043:91–6.
Vos et al(1994) Biochem Biophys Acta1211:125–49.
Wahees and Van Etten(1985) Biochem Biophys Acta 831:67–73.
Wenger and Louie(1991) Neurosci 13:216–21.
Widzowski and Cory–Slechta(1994) Neurotoxicology 15:295–308.

*Primary Examiner*—Scott W. Houtteman
*Attorney, Agent, or Firm*—Klauber & Jackson

[57] ABSTRACT

The present invention relates to methods for diagnosis of susceptibility to neurotoxicity or the pathological effects of neurotoxicity based on detection of a genetic marker in an individual. The present invention is directed generally to methods and associated compositions and kits for detecting the presence of arylsulfatase A (ASA) pseudodeficiency (PD) mutations in humans. Detection of these mutations has been surprisingly found to be a strong indicator for susceptibility to neurotoxicity and/or susceptibility to toxicant's pathological effects, as well as an important marker in evaluating the likelihood of metachromatic leukodystrophy (MLD).

26 Claims, 5 Drawing Sheets

FIG. 4A
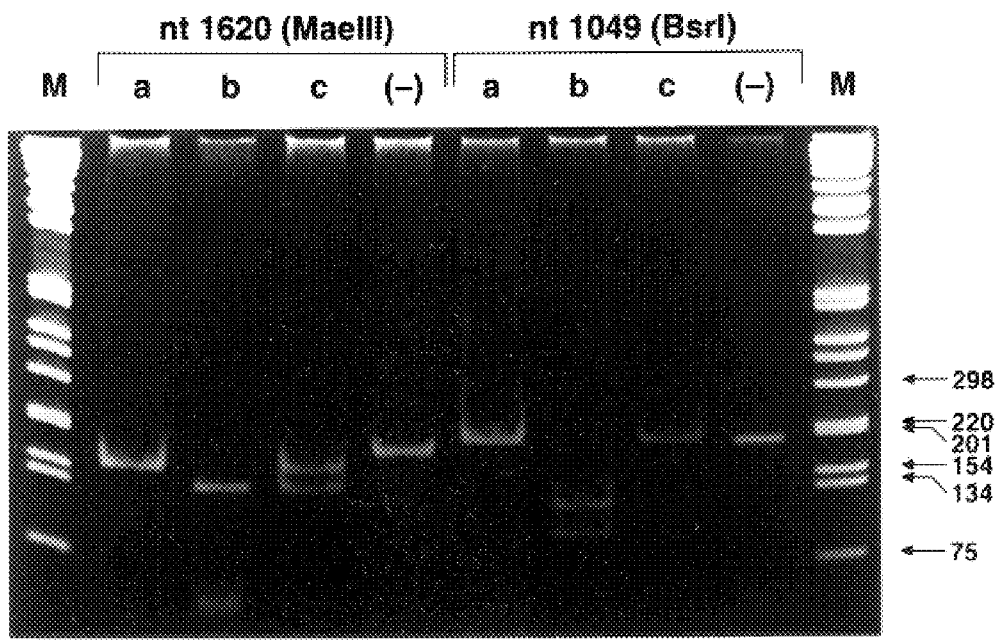
FIG. 4B
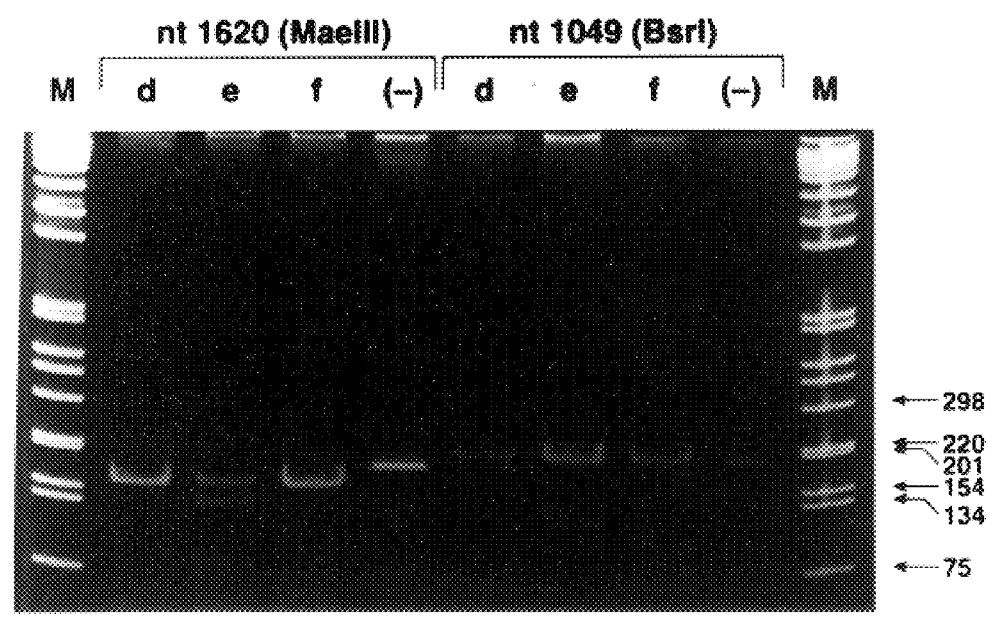
FIG. 4C
|  | SUBJECTS | | | | | |
| --- | --- | --- | --- | --- | --- | --- |
|  | a | b | c | d | e | f |
| PolyA signal site | -/- | +/+ | +/- | -/- | +/- | -/- |
| N-glycosylation site | -/- | +/+ | +/- | -/- | +/- | +/- |

FIG.5A
N-Glyc. (BsrI)
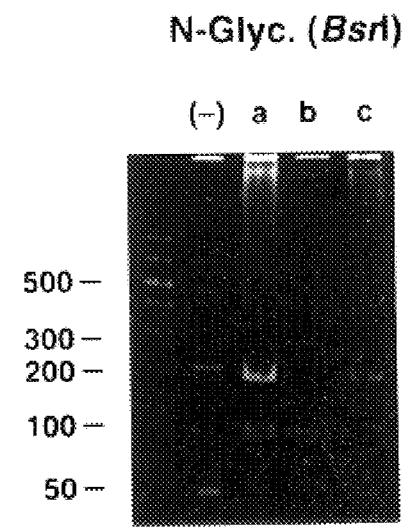
FIG.5B
PolyA (MaeIII)
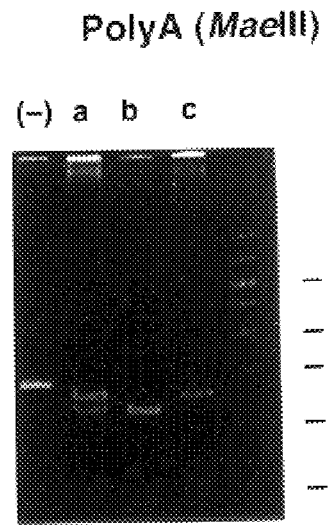
FIG.5C
N-Glyc. (BsrI)
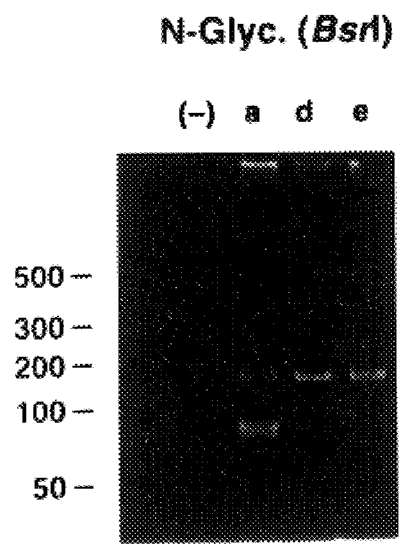
FIG.5D
PolyA (MaeIII)
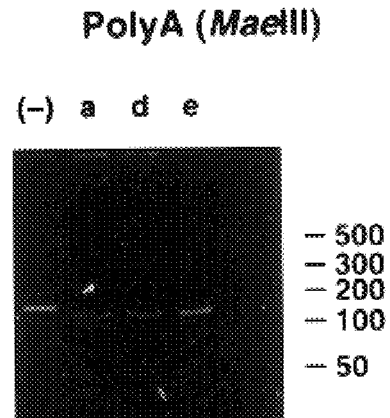
FIG.5E
| | SUBJECTS | | | | |
|---|---|---|---|---|---|
| | a | b | c | d | e |
| PolyA signal site: | +/– | +/+ | –/– | –/– | –/– |
| N-glycosylation site: | +/– | +/+ | –/– | +/– | –/– |

METHOD FOR DETECTING A PREDISPOSITION TO SUSCEPTIBILITY TO TOXIC EFFECTS OF DRUGS AND POISONS

This application claims the benefits of U.S. Provisional Application No. 60/022,493 filed Aug. 06,1996.

FIELD OF THE INVENTION

The present invention relates to methods for diagnosis of susceptibility to neuropathologies caused by toxicants based on detection of a genetic marker in an individual that identifies a partial deficiency of lysosomal enzymes. More particularly, the present invention relates to the relationship of inherited, partial deficiencies of lysosomal enzymes and susceptibility to pathologies caused by toxicants, such as lead, lysosomotropic pharmaceuticals, and other neuroactive agents. A genetic factor which may cause certain individuals to be hypersusceptible has been identified. The understanding of this genetic factor allows for a more detailed dissection of the biochemical processes involved in neuropathologies. A consequence of this development is the identification of individuals in an at risk population who are hypersusceptible to neurotoxicity and therefore, may be targeted for treatment.

BACKGROUND OF THE INVENTION

Early studies showed that arylsulfatase A (ASA) electrophoresed in native polyacrylamide gels and stained for enzymatic activity exhibited a variety of electrophoretic patterns, some of which were more likely to be found in alcoholic patients than in non-alcoholic psychiatric and normal control subjects [Hulyalkar et al., *Alcoh.: Clin. Exp. Res.* 8:337–341 (1984)]. However, lacking any biochemical explanation for these observations, no correlation with a genetic basis or marker for alcoholism was possible.

A more severe neuropathological disease associated with a deficiency of ASA is metachromatic leukodystrophy (MLD). MLD is a debilitating genetic disease characterized by neuropsychological deficits. In late-onset MLD, the initial symptoms include attentional difficulties, hyperactivity, impulsivity, poor judgement, and emotional lability [Shapiro et al., *Neurology* 44:662–665 (1994)]. MLD patients display a characteristic demyelination pathology resulting from increased levels of sulfatides. This glycolipid comprises a significant proportion of the myelin sheath and accumulates in various tissues of individuals with MLD. MLD is caused by the lack of the enzyme activity of arylsulfatase A (ASA, EC 3.1.6.8), a lysosomal glycoprotein which catalyzes the desulfation of sulfatides, the first step in sulfatide catabolism.

Some individuals exhibit much reduced levels of ASA activity, but appear to catabolize sulfatides adequately and lack apparent MLD-related neurological symptoms [Kolodny, E. H., *The Metabolic Basis of Inherited Disease*, eds., pp. 1721–1750 (1989)]. These people are pseudodeficient for ASA (PD-ASA) and possess an ASA gene which has two A-G transitions. One of these mutations results in an $Asn_{350}$ to Ser conversion, causing a loss of a potential N-glycosylation site, and the other in a polyadenylation signal consensus sequence alteration, resulting in a reduction of a 2.1 Kb message [Gieselmann et al., *Proc. Natl. Acad. Sci. USA* 86:9436–9440 (1989)]. The PD-ASA gene frequency, at approximately 10%, is quite common [Nelson et al., *Hum. Genet.* 87:87–88 (1991)]. A number of multiband electrophoretic variants of ASA are found in the general population [Poretz, et al., *Biochem. J.* 287:979–983 (1992)]. Previous work demonstrated that the electrophoretic (non-denaturing) pattern is due to a heterogeneous mixture of ASA isoforms with variable degrees of phosphorylation of the N-glycan moieties, and hypothesized that the variant forms may reflect differences in both the structure of the carbohydrate units and polypeptide of the enzyme [(Poretz et al., supra; Park et al., *Alcohol. Clin. Exper. Res.* 20:234–239 (1996)].

The pseudodeficiency mutations do not cause MLD but reduce the enzyme activity of ASA sufficiently to complicate the diagnosis of MLD and MLD carrier status in families where they occur [Wenger & Louie, *Dev. Neurosci.*, 13:216–221 (1991)]. While the polyadenylation signal sequence mutation has been proposed to be the cause of the reduced ASA activity in pseudodeficiency [Gieselmann et al., supra (1989)], there is evidence that the N-glycosylation site mutation reduces ASA enzyme activity to a greater extent [Shen et al.,*Am. J. Med. Genet.,* 45:631–637 (1993)1. This is significant as the N-glycosylation site mutation can occur in the absence of the polyadenylation signal site mutation (Nelson et al., supra; Shen et al., supra]. The ability to distinguish this mutation is therefore important in diagnosis and risk determination in families with MLD [Shen et al., supra; Park et al., supra (1996)].

Previously, allele specific tests have been described [Gieselmann et al., supra (1989); Gieselmann et al., *Hum. Genet.* 86:251 (1991)]. However, no clear relationship between neurologic disease and enzyme deficiency has been conclusively established [Kolodny, in Metabolic Basis of Inherited Disease, Vol. II, C. R. Scriber et al. (Eds.), McGraw-Hill: New York. pp. 1721–1740 (1989)]. In particular, homozygosity for the PD-ASA allele has been reported to bear no clinical consequence, and that homozygosity for the PD-ASA allele is no more frequent among neuropsychiatric patients than normal controls [Hohenschutz et al., *Am. J. Med. Genet.* 31:169–175 (1988)]. Individuals who present with an $ASA^{negative}$/PD-ASA genotype (i.e., heterozygous MLD) may have a greater incidence of clinical abnormalities [Hohenschutz et al., *Hum. Genet.* 82:4548 (1989)]. A more recent publication disputes this hypothesis [Penzien et al., *Am. J. Hum. Genet.* 52:557–564 (1993)].

An important breakthrough in the prevention of alcoholism came with the recognition that homozygosity for the PD-ASA allele is associated with a predisposition to alcoholism (International Patent Publication WO 96/07098, published Mar. 7, 1996, by Manowitz et al.; U.S. patent application Ser. No. 08/299,187 filed Aug. 31, 1994; provisional U.S. Patent Application No. 60/001,300, file Jun. 21, 1995; and U.S. application Ser. No. 08/666,029, filed Jun. 19, 1996; each of which is incorporated herein in its entirety). This discovery represented the first identification of a genetic association of ASA with alcoholism. Previously, biochemical differences in ASA (i.e., the extent of glycosylation) were attributed to the effects of alcohol on protein processing and glycosylation. In particular, homozygosity for a mutation in a residue 350 N-glycosylation site of ASA, or both this mutation and a mutation of the polyadenylation signal sequence, correlates with greater susceptibility to alcoholism. The data presented in that publication demonstrate that humans who are homozygous for a genetic mutation of ASA that results in absence of an N-linked glycan at amino acid residue 350 of ASA are approximately 8 to approximately 18 times more likely to be found with alcoholics than non-alcoholic individuals.

Lead-Induced Neuropathologies

Lead-induced neurotoxicity has a long medical history [Nriagu, in *Human Lead Exposure.* Ed. H. L. Needleman.

CRC Press, Boca Raton, Fla. pp 3–21 (1992); Lin-Fu, *Human Lead Exposure*. Ed. H. L. Needleman. CRC Press, Boca Raton, Fla. pp 2343 (1992)), and is still a major concern, especially with children [Rosen, *Toxicology* 97:11–17 (1995); Bellinger and Needleman, *Human Lead Exposure*. Ed. H. L. Needleman. CRC Press, Boca Raton. Fla. pp 191–208 (1992); Schwartz, *Human Lead Exposure*. Ed. H. L. Needleman. CRC Press, Boca Raton, Fla. pp 223–242 (1992); Gatsonis and Needleman, *Human Lead Exposure*. Ed. H. L. Needleman. CRC Press, Boca Raton, Fla. pp 243–255 (1992); Needleman, *Neurotoxicology* 322:83–88 (1993)]. Though environmental levels of lead have dropped precipitously in recent years, no threshold level of toxicity is apparent, suggesting that prevailing levels may be greater than those resulting in neurotoxicity [Schwartz, *Environ. Res.* 54:42–55 (1994)] and that prenatal exposure may have long lasting developmental effects [Lin-Fu, supra; Bellinger and Needleman, supra; Schwartz, supra]. Lead toxicity is a broad spectrum and possibly a multifactorial product of ingested and absorbed lead (Pounds and Cory-Slechta, *Neurotoxicology* 14:4–6 (1993); Grandjean, Neurotoxicology 14:9–14 (1993)]. The dose-response relationship for lead neurotoxicity is complex and may be related in part, to individual resistance and susceptibility parameters [Bellinger and Needleman, supra; Pounds and Cory-Slechta, supra; Grandjean, supra]. Accordingly, the characteristics of the neuropathologies are quite varied. Lead's impact may vary from observed severe encephalopathies [Marsh, *Neurotoxicity of Industrial and Commercial Chemicals*, Ed. J. L. O. Donohue. CRC Press, Boca Raton. Fla., pp. 159–169 (1985); Duncan, *Neurotoxicity of Industrial and Commercial Chemicals*, Ed. J. L. O. Donoghue. CRC Press, Boca Raton, Fla., pp. 15–50 (1985)] to more subtle dysfunctions such as cognitive and behavioral disorders (Ruff et al., 1993; Needleman et al., *N. Eng. J. Med.* 322:83–88 (1990); Bellinger and Needleman, supra; Gatsonis and Needleman, supra; Cohn et al., *Neurotoxicology* 14:329–346 (1993); Rice, *Neurotoxicology* 14:167–178 (1993); Bellinger et al., *Environ. Res.* 66:12–30 (1994)]. Though rarely seen today in the U.S., severe lead poisoning can result in acute encephalopathy characterized by cerebral edema and focal cerebellar atrophy with little evidence for primary myelin damage and presenting with the symptoms of ataxia, coma and convulsions [Pentschew, *Acta Neuropathol.* 5:133–160 (1965); Marsh, supra; Duncan, supra]. Chronic exposure to lower levels of lead produce peripheral neuropathy, principally as segmental demyelination probably due to primary damage to the myelin forming glial cells [Duncan, supra, Silbergeld, *Human Lead Exposure*. Ed. H. L. Needleman. CRC Press, Boca Raton, Fla. pp 89–103 (1992)], giving rise to abnormalities of visual/motor and fine motor control with evidence of slower median nerve conduction velocity [see Silbergeld, 1992, supra], and also resulting in symptoms of fatigue, irritability, headaches and short-memory deficits [see Silbergeld, 1992, supra]. Chronic, "relatively low" levels of lead exposure, especially during the prenatal and early neurodevelopmental formative years, causes cognitive deficits, and abnormal verbal, perceptual, and motor function as measured by a number of criteria [Ruff et al., *JAMA* 269:1641–1646 (1993); Bellinger and Needleman, supra, Schwartz, supra; Lilienthal et al., *Environ. Health Perspect.* 89:21–25 (1990); Murshak et al., *Environ. Res.* 50:11–36 (1989)] and often evidenced as learning and behavioral problems in affected children [Bellinger and Needleman, supra; Bellinger et al., supra; Schwartz, supra; Murshak et al., supra].

Mechanisms of Lead-Induced Neurotoxicity

It has been shown that lead, which impacts on virtually all organs, affects numerous biochemical pathways [Pounds and Cory-Slechta, supra; Silbergeld, 1992, supra; Bressler and Goldstein, *Biochem. Pharmacol.* 41:47–484 (1991); Wedeen, *Human Lead Exposure*. Ed. H. L. Needleman. CRC Press, Boca Raton, Fla. pp 169–189 (1992)] and can interact with thiol containing proteins [Goering, *Neurotoxicology* 14:45–60 (1993)]. The molecular toxicology of lead-induced neuropathies is open to conjecture, and a number of plausible mechanisms have been advanced. The chemical similarities of lead and calcium, and to some degree zinc, have led to a number of proposals stating that lead is capable in some biochemical reactions of acting synergistically or competitively with calcium or zinc to either potentiate or inhibit reactions requiring or involving these physiologically important divalent metals (Bressler and Goldstein, supra; Goering, supra; Simons, *Neurotoxicology* 14:77–86; Goldstein, *Human Lead Exposure*. Ed. H. L. Needleman. CRC Press, Boca Raton, Fla. pp 125–135 (1993) and *Neurotoxicology* 14:97–104 (1993)].

The literature [see Goering, supra] supports the contention that lead can displace zinc from δ-aminolevulinic acid dehydrase causing inactivation of the enzyme and inhibition of normal heme synthesis. It has been suggested that both the decrease of available heme formation for maintenance of necessary levels of vital heme proteins, and the accumulation of δ-aminolevulinic acid, which may act as a neuroactive agent, may affect neurodevelopment [see Silbergeld, 1992, supra]. It is now well appreciated that calcium mediated regulatory pathways are vital for normal cellular activity (Ghosh and Greenberg. *Science* 268:239–247 (1995); Hanson and Schulman. *Annu. Rev. Biochem.* 61:559–601 (1992)] and can be targets for lead-induced toxicity [Goering, supra; Goldstein, 1993. supra; Silbergeld, 1992, supra]. Accordingly, lead may have profound effects on numerous, apparently unrelated biochemical pathways and cellular events affecting either neuronal survival and/or formation of effective cell-cell connections, as well as maintenance of a normal blood-brain barrier. Lead has been shown to stimulate basal neurotransmitter release, possibly through calcium-related mechanisms, in both the peripheral and central nervous system and causes inhibition of evoked release of neurotransmitters in the CNS [see Silbergeld, 1992, supra; Goldstein, 1993, supra]. Given the trophic effects of modulated neurotransmitter release, the impact of this process on the formation of synaptic connections, especially in the early developing brain, has been proposed to explain the impact of lead upon cognitive and behavioral characteristics of children exposed to low levels of the metal [Goldstein, 1993, supra; Silbergeld, 1992, supra; Kern et al., *Neurotoxicology* 14:319–328 (1993)]. Related to this, others (Regan, *Neurotoxicology* 14:69–76 (1993); Reuhl et al., *Neurotoxicology*, 15:133–145 (1994); Lagunowich et al., *Neurotoxicology* 15:123–132 (1994)] have suggested that lead may affect processes important for the proper synthesis and function of necessary neural cell surface glycoconjugates resulting in abnormal neuronal cell-cell interactions, thereby altering normal synaptic development.

Given the potential number of biochemical pathways which may be affected by lead, it is noteworthy that to date, no hereditary risk factors related to lead-induced neurotoxicity have been identified other than a recent report of a weak association of ALAD-2 genotype with the pharmacokinetic and toxicity parameters of lead in adults [Smith et. al., *Environ. Health Perspect.* 103:248–253 (1995)].

Arylsulfatase A Deficiencies

Some individuals with congenital forms of reduced levels of arylsulfatase A (ASA) exhibit neurobehavioral symptoms similar to those observed in children exposed to chronic, low levels of lead. A profound deficiency (less than 5–10% normal levels) of this ubiquitous lysosomal enzyme results in the fatal neurodegenerative condition, metachromatic leukodystrophy (MLD) [Kolodny and Fluharty, in The Metabolic and Molecular Basis of Inherited Disease, Ed. C. R. Scriver. McGraw-Hill, New York, pp. 2693–2739 (1995)]. However, individuals with reduced, but significant residual levels of the enzyme (10–20% normal levels) may exhibit behavioral and cognitive difficulties prior to the detection of overt neurological deficits [Kolodny and Fluharty, supra; Shapiro, supra]. This enzyme desulfates the glycolipid, sulfatide, and produces galactosylceramide. Proper levels of both glycolipids are required for normal neurodevelopment, and significant sulfatide synthesis occurs predominantly in oligodendrocytes, Schwann cells and kidney (Kolodny and Fluharty, supra; Vos et al., *Biochim. Biophys. Acta* 1211:125–149 (1994)]. In particular, levels of sulfatide appear to be regulated during critical stages of early nervous system development (Vos et al., supra; van der Pal et al., *Biochim. Biophys. Acta* 1043:91–96 (1990)].

Three forms of MLD, related to the age of the patient at onset, correlate with the amount of the patient's residual sulfatase activity [see Kolodny and Fluharty, supra]. Late infantile MLD is recognized at age 2 and is fatal within a few years. The juvenile form is evident between ages 4–12, and the adult form is diagnosed between the teen-age years and 80 years of age. Mental confusion, cognitive difficulties, gait disturbance and mental regression are early indicators of the late-onset forms of the condition caused by reduced ASA levels. Major presenting early signs of the adult, late-onset form include behavioral problems such as attentional deficits, hyperactivity, impulsivity, poor judgement, and emotional lability [Shapiro, supra]. These early behavioral symptoms precede any evidence of de- or dysmyelination, which result in detectable neurological symptoms. Evidence [Meier and Bischoff, *Acta Neuropathol.* 36:369–379 (1976); Argyrakis et al., *Neuropathol. Exper. Neurol.* 36:693–711 (1977); see Kolodny and Fluharty, supra] suggests that demyelination or dysmyelination associated with this condition is preceded by affected cells containing abnormal levels of multilaminar lysosomal structures believed to be associated with the process of demyelination [Brun and Brunk, *Acta Pathol. Microbiol. Scand.* 82:311–318 (1974); Coria et al., *J. Submicrosc. Cytol.* 18:153–159 (1986)]. Though the molecular mechanism by which elevated levels of sulfatide cause demyelination and other neurobehavioral abnormalities is unknown, this glycolipid is important to a number of vital processes for cells of the nervous system, including: cell adhesion [Vos et al., supra] calcium-mediated signaling pathways [Dyer and Benjamins, *J. Neurosci. Res.* 30:699–711 (1991); Dyer, *Mol. Neurobiol.* 7:1–22 (1993)]; and the $Na^+/K^+$ ATPase implicated in neuropathologies [Lees, *Brain Res. Rev.* 16:283–300 (1991); see Kolodny and Fluharty, supra]. Accordingly, reduced levels of ASA may result in a pleiotropic effect. Abnormal sulfatide levels may affect biochemical pathways involved in neurodevelopment independent of, and in addition to, those processes leading to de- and dysmyelination. The extent of the pleiotropism and determination of the involved pathways may be dependent upon the levels of sulfatide and the stage of neurodevelopment of the individual. Some individuals have an inherited form of ASA which results in reduced levels of the enzyme. These people do not display overt neurological symptoms of MLD, but may exhibit neurobehavioral abnormalities.

Pseudodeficient ASA

The gene for ASA possesses a set of polymorphic sequences. Certain mutant forms of these sequences, when in the homozygous state, may cause reduced intracellular steady-state levels (15–25% of normal) of ASA, when tissue extracts are measured for ASA activity using a water soluble synthetic substrate such as p-nitrocatechol sulfate. This inherited abnormality is called pseudodeficiency of ASA (PD-ASA) and was characterized at the molecular level, initially as being caused by two separate A→G transitions at base residues 1788 and 2723 [Gieselmann et al., supra (1989); see Kolodny and Fluharty, supra]. The former mutation is in the coding region and causes a change in the protein sequence, resulting in $Asn_{350}$ being converted to Ser. This mutation eliminates a potential N-glycosylation site which is utilized in the normal protein [Gieselmann et al., supra (1989); Sommerlade et al., *J. Biol. Chem.* 269:20977–20981 (1994); Park et al., *Alcoholism: Clin. Exper. Res.* (1995); see Kolodny and Fluharty, supra] and causes an altered mobility in native PAGE [Poretz et al., supra; Park et al., 1995, supra and Park et al., *Biochem. Genet.,* (1995)]. The other mutation is in the non-coding portion of the gene, and destroys a potential polyadenylation signal site sequence for the major RNA message of the gene [Gieselmann et al., supra (1989); see Kolodny and Fluharty, supra]. The result of the Asn350→Ser mutation gives rise to an abnormally glycosylated form of ASA which has an intracellular half-life of only 20–25% of the normal enzyme [Ameen and Chang, *FEBS Lett.* 219:130–134 (1987)]. The polyadenylation signal site mutation causes decreased levels of message and results in a 20–50% reduction in the rate of synthesis of ASA in fibroblasts from individuals with this polymorphism [Ameen and Chang, supra; Gieselmann et al., supra (1989)]. The sum of the effects of both mutations causes the levels of ASA in individuals presenting with PD-ASA to be as low as 15–25% that of normal. However, it is evident that the N-glycosylation site mutation is the dominant factor resulting in these reduced levels of ASA.

Approximately 35.1% of Caucasian-Americans carry the N-glycosylation site polymorphism of PD-ASA, of which approximately 9 million Caucasian-Americans (4.8% of 190 million) are homozygous for this mutation. Twenty-three percent of these individuals have the double mutation. It is particularly noteworthy that 60.3% of African-Americans and 55.1% of Black Canadians [Ott et al., *Am. J. Hum. Genet.* 55:160A (1994)] carry the N-glycosylation site mutation, but rarely exhibit the polyadenylation signal site mutation. Accordingly, 14% (approximately 5 million) of the African-Americans are homozygous for the abnormally glycosylated form of ASA, thereby resulting in these individuals having reduced levels of ASA activity.

The citation of any reference herein should not be deemed as an admission that such reference is available as prior art to the present invention.

SUMMARY OF THE INVENTION

The present invention is directed generally to methods and associated compositions and kits for detecting the presence of arylsulfatase A (ASA) pseudodeficiency (PD) mutations in humans. Detection of these mutations has been surprisingly found to be a strong indicator for susceptibility to neurotoxicity and/or susceptibility to toxicants' pathological effects. In specific examples, the invention relates to detection of susceptibility to lead toxicity.

Accordingly, in a first aspect, the invention is directed to a method for identifying an individual who may be susceptible to neurotoxicity or to the pathological effects of toxicants comprising identifying whether an individual is homozygous, heterozygous, or normal for a pseudodeficiency (PD) mutation in the arylsulfatase A (ASA) gene, wherein heterozygosity for a PD mutation indicates that the individual may exhibit increased susceptibility to neurotoxicity, and homozygosity for a PD mutation in each allele of the ASA gene indicates that the individual may be more susceptible to neurotoxicity than the heterozygous individual. In particular, the invention relates to detecting a mutation in a residue 350 N-glycosylation site of ASA, or to detecting a mutation in a polyadenylation signal sequence of at least one allele of ASA, or to detecting both mutations in an ASA allele. Thus, an individual who is heterozygous PD/normal is at increased risk, relative to normal individuals, for susceptibility to neurotoxicity; and an individual who is homozygous for the PD mutation is at greatly increased risk for susceptibility to neurotoxicity.

The methods of the invention are advantageously carried out using polymerase chain amplification (PCR) analysis. Preferably, the PCR product of the mutant and normal ASA can be differentiated by specific restriction endonucleases. In a specific embodiment, the PCR analysis for the mutation in the residue 350 N-glycosylation site can be performed by amplifying an approximately 200-base pair segment of genomic DNA with a 5' primer TGATGGCGAACTGAGTGACT (SEQ ID NO:9) and a 3' primer AAGGATCTGGGATCAGGGGT (SEQ ID NO:10); and detecting the presence of a BsrI restriction endonuclease site; wherein the BsrI endonuclease site is present in the PD mutant ASA allele. More preferably, a 5' primer CACCCCAACCTTGATGGCGAACTGGGTGAC (SEQ ID NO:14) and a 3' primer AAGGATCTGGGATCAGGGGT (SEQ ID NO:10) are used. The 5' primer generates a 211 base pair fragment spanning the third potential N-glycosylation site at amino acid residue 350, but has been modified by substitution of a G for A to as to introduce a BsrI site 25 nucleotides from the 5' end, which acts as a control for BsrI activity. The presence of two BsrI restriction endonuclease sites is indicative of the mutation; the presence of only one site is indicative of wild type; and the presence of no BsrI site indicates that the experiment has not yielded a meaningful result.

In another specific embodiment, the analysis for the mutation in the polyadenylation signal sequence can be performed by amplifying about an approximately 182-base pair segment of genomic DNA with a 5' primer AGCTTGCTGCCATTGCCCA (SEQ ID NO:11) and a 3' primer CATTACCCCAGGATTGGTCGAA (SEQ ID NO:12); and detecting the presence of two MaeIII restriction endonuclease sites; wherein two MaeIII endonuclease sites are present in the PD mutant ASA allele.

Alternatively, the PCR product can be probed with probes specific for the wild type (normal) and mutated sequences of ASA gene. In a specific embodiment, a segment of genomic DNA or mRNA containing the N-glycosylation site is amplified by PCR, and analyzed by hybridization of an oligonucleotide probe selected from the group consisting of AAGGTGACATTGGGCAGTGG (SEQ ID NO:5) and AAGGTGACACTGGGCAGTGG (SEQ ID NO:6) to the amplified sequence, wherein hybridization of the former probe at 55° C. with washing at 62° C. is indicative of a normal ASA allele, and hybridization of the latter probe at 55° C. with washing at 60° C. is indicative of a PD allele. In another specific embodiment, a segment of genomic DNA containing the polyadenylation signal site is amplified by PCR, and analyzed by hybridization of an oligonucleotide probe selected from the group consisting of CTGGTGT-TATTACGTTATC (SEQ ID NO:7) and CTGGTGTTACTACGTTATC (SEQ ID NO:8) to the amplified sequence, wherein hybridization of the former probe at 48° C. with washing at 52° C. is indicative of a normal ASA allele, and hybridization of the latter probe at 48° C. with washing at 52° C. is indicative of a PD allele.

A particular advantage of the present invention is that the PCR analysis can be performed on DNA obtained from buccal cells. Preferably, the analysis involves identification of restriction endonuclease sites unique to either the mutant ASA or native (wild type) ASA, or both.

The invention further provides for detecting mutant ASA lacking an N-glycan moiety by biochemical analysis. In a specific embodiment, the biochemical analysis comprises detecting a difference in the relative electrophoretic mobility of an ASA protein from an individual possessing the mutant ASA enzyme as compared to a normal ASA protein.

In a preferred aspect, the mutation in the N-glycosylation site is detected by immunochemical analysis. For example, the immunochemical analysis can comprise detecting binding of an antibody specific for an epitope of ASA lacking an N-glycosylation site, wherein the antibody does not bind to normal ASA. In a preferred embodiment, the antibody is a monoclonal antibody; in a specific Example, preparation of such an antibody against the peptide Ac-CAPLPSVTLDGFD-NH$_2$ (SEQ ID NO:13) is described.

To characterize whether an individual is homozygous for the PD alleles of ASA, heterozygous, or homozygous for normal ASA, an antibody assay of the invention contemplates comparing the amount of ASA bound by an antibody specific for the PD mutant ASA to the amount of ASA bound by an antibody that binds to all forms of ASA. If the quantity of ASA bound by the antibody specific for the mutant ASA is about the same as the quantity bound by the antibody reactive with all ASA, then the individual is homozygous for the PD alleles; if the amount of ASA bound by the mutant-specific antibody is about half the amount bound by the antibody reactive with all forms of ASA, then the individual is heterozygous; and if the amount of ASA bound by the mutant-specific antibody is much less than the amount bound by the antibody reactive with all forms of ASA, then the individual is homozygous normal.

Accordingly, the invention relates to an antibody specific for an epitope of ASA lacking an N-glycosylation site, wherein the antibody does not bind to normal ASA containing the N-glycosylation site. Preferably, the antibody is a monoclonal antibody, e.g., a murine monoclonal antibody generated against the peptide Ac-CAPLPSVTLDGFD-NH$_2$ (SEQ ID NO:13).

The invention further provides kits for identifying an individual who is susceptible to neurotoxicants or to the pathological effects of such toxicants. One such kit comprises the antibody described above, an antibody specific for all forms of ASA; and means for quantitating binding of the antibody specific for an epitope of mutant ASA and the antibody specific for all forms of ASA to ASA in a sample from an individual.

In another embodiment, the invention relates to a method for identifying an individual carrying a pseudodeficiency (PD) mutation of an allele of an arylsulfatase A (ASA) gene, comprising detecting a mutation in a residue 350 N-glycosylation site of at least one allele of ASA by polymerase chain amplification (PCR) analysis, wherein the PCR product of the mutant and normal N-glycosylation site can be differentiated by specific restriction endonucleases.

In a further aspect, the invention also relates to a method for identifying an individual carrying a PD mutation of an allele of an ASA gene, comprising detecting a mutation in a polyadenylation signal sequence of at least one allele of ASA by PCR analysis, wherein the PCR product of the mutant and normal polyadenylation signal sequence can be differentiated by specific restriction endonucleases. In yet another aspect, the invention relates to a method for identifying an individual carrying a PD mutation of an allele of an ASA gene comprises detecting a mutation in a residue 350 N-glycosylation site of at least one allele of ASA by polymerase chain amplification (PCR) analysis, wherein the PCR product of the mutant and normal N-glycosylation site can be differentiated by specific restriction endonucleases; and detecting a mutation in a polyadenylation signal sequence of at least one allele of ASA by polymerase chain amplification (PCR) analysis, wherein the PCR product of the mutant and normal polyadenylation signal sequence can be differentiated by specific restriction endonucleases. In a preferred embodiment, the specific probes and endonucleases described above are used.

A kit for identifying an individual who is susceptible to neurotoxicity or to the pathological effects of toxicants, or for evaluating whether the individual has a PD allele of ASA, comprises a 5' primer having the sequence TGATG-GCGAACTGAGTGACT (SEQ ID NO:9) or, more preferably, a 5' primer CACCCCAACCTTGATGGC-GAACTGGGTGAC (SEQ ID NO:14) and a 3' primer having the sequence AAGGATCTGGGATCAGGGGT (SEQ ID NO:10) and a BsrI restriction endonuclease; or a 5' primer having the sequence AGCTTGCTGCCATTGCCCA (SEQ ID NO:11) and a 3' primer having the sequence CATTACCCCAGGATTGGTCGAA (SEQ ID NO:12) and a MaeIII restriction endonuclease, or both.

Accordingly, the invention provides an oligonucleotide selected from the group consisting of TGATGGCGAACT-GAGTGACT (SEQ ID NO:9); AAGGATCTGGGAT-CAGGGGT (SEQ ID NO:10); AGCTTGCTGCCATTGC-CCA (SEQ ID NO:11); CATTACCCCAGGATTGGTCGAA (SEQ ID NO:12); and CACCCCAACCTTGATGGCGAACTGGGTGAC (SEQ ID NO:14).

Thus, it is an object of the invention to provide convenient methods and reagents for identifying individuals who are carry one or two PD alleles of the ASA gene.

A particular object of the invention is to identify individuals who may have a greater susceptibility to neurotoxicity, or to the pathological effects of toxicants, or both.

Another object of the invention is to provide methods and reagents to more easily detect the mutations characteristic of the PD alleles of ASA, which can be used for genetic counselling.

These and other objects of the present invention will be made more clear by reference to the following drawings and detailed description of the invention.

BRIEF DESCRIPTION OF THE DRAWINGS

FIG. 4A–C. Detection of the pseudodefilciency mutations of ASA. (A) DNA from blood leukocytes of three individuals (a, b and c) was amplified across the polyadenylation site of ASA (nucleotide 1620 of the cDNA) and treated with MaeIII or amplified across the position 350 N-glycosylation site of ASA (position 1049 of the cDNA) and cut with BsrI, as indicated. The lanes indicated (−) represent the amplified DNA product not treated with restriction enzyme. M, DNA size markers, in base pairs (1 kb ladder, Gibco-BRL). nt=nucleotide position in the ASA cDNA [Stein et al., *J. Biol. Chem.*, 264:1252–1259 (1989)]. The DNA products and size markers are separated by electrophoresis through 7.5% polyacrylamide gels. (B) DNA from buccal cells of three other individuals (d, e and f), amplified and treated with restriction enzymes and analyzed as in A. (C) Summary of the DNA analysis of the pseudodeficiency mutations of ASA from subjects analyzed in A and B. The presence (+) or absence (−) of the mutation at each site is indicated for the two alleles.

FIG. 5A–E. Detection of the pseudodeficiency mutations of ASA. DNA from leukocytes or buccal cells (or in the case of a, both) of five subjects was amplified and analyzed for the presence of specific restriction endonuclease sites. In lanes marked (−), the amplified DNA was not treated with the endonuclease. The size of some bands in the DNA marker lanes is indicate in base pairs. (A) Amplification of leukocyte DNA across the N-glycosylation site (nucleotide 1049) and cut with BsrI. (B) Amplification of leukocyte DNA across the polyadenylation signal site (nucleotide 1620) and cut with MaeIII. (C) Amplification of buccal cell DNA across the N-glycosylation site. (D) Amplification of buccal cell DNA across the polyadenylation signal site. (E) ASA genotypes of the subjects analyzed.

DETAILED DESCRIPTION OF THE INVENTION

Figure 1:
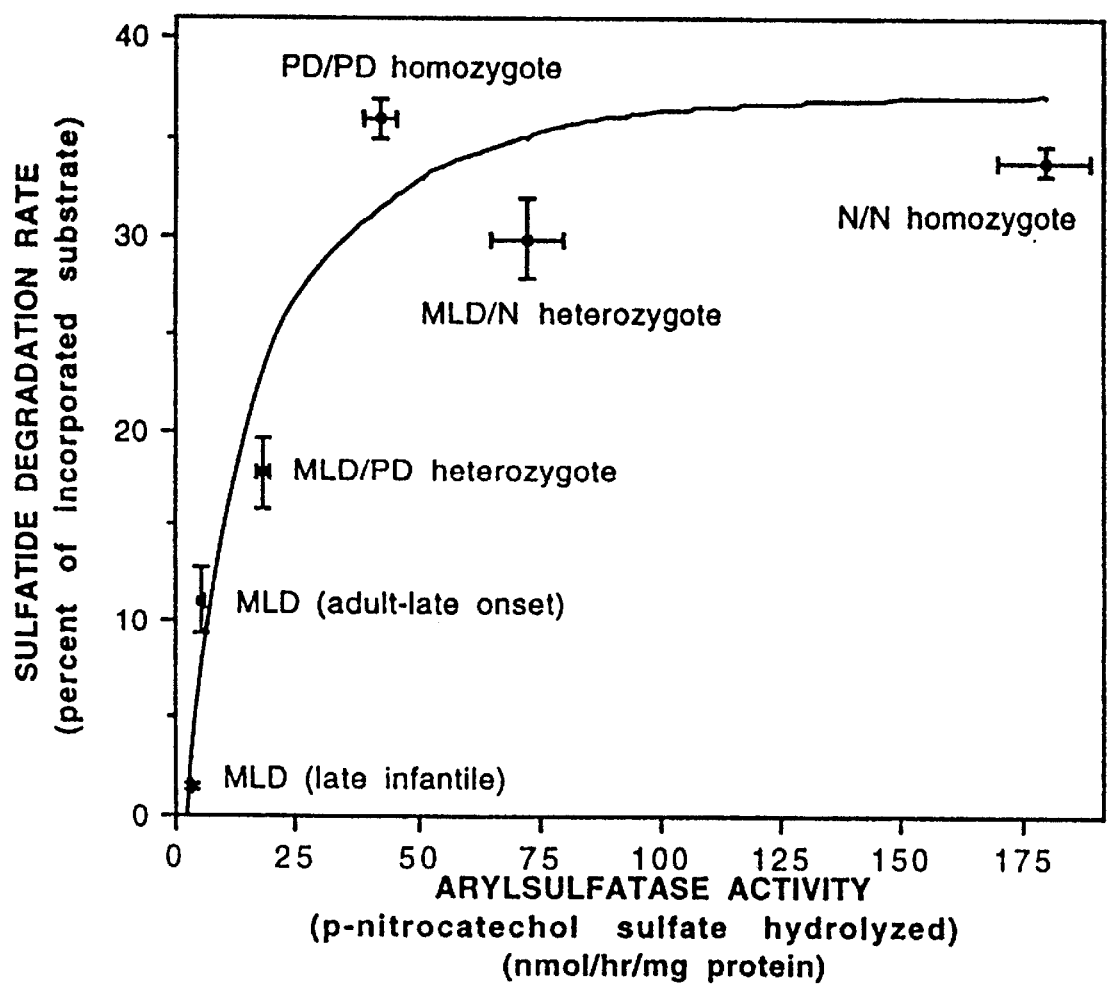
FIG. 1. PRIOR ART: The relationship of cellular levels of ASA enzymic activity with respect to the ability of fibroblasts to degrade sulfatide in a sulfatide loading test. Each data point is the mean value (showing s.e.m. limits) obtained for between 10 and 20 subjects in each genotypic or phenotypic group. This figure is a representation of the data published by Conzelmann and Sandhoff (1991).

In its broadest aspect, the present invention is based on the discovery that mutations characteristic of pseudodeficiency (PD) of the arylsulfatase A (ASA) gene are indicative of susceptibility to neurotoxicity or to the pathological effects of toxicants, or both. The effect of the ASA gene is dose related. Thus, a heterozygous PD/normal mutation results in increased susceptibility to toxicants as compared to the normal homozygous state. In particular, the occurrence of homozygosity for the PD abnormality which results in expression of ASA lacking the N-glycosylation site at residue 350 is even more strongly correlated with neurotoxicity; homozygous PD individuals have greater susceptibility to toxicants than heterozygous PD/normal individuals.

Thus, the present invention relates to the relationship of inherited, partial deficiencies of lysosomal enzymes and susceptibility to pathologies caused by toxicants, such as lead-induced neurotoxicity, lysosomotropic pharmaceuticals, and other neuroactive agents. A genetic factor which may cause certain individuals to be hypersusceptible has been identified. The understanding of this genetic factor allows for a more detailed dissection of the biochemical processes involved in neuropathologies. A consequence of this development is the identification of individuals in an at risk population who are hypersusceptible to neurotoxicity and therefore, may be targeted for treatment. More particularly, heterozygous PD/normal individuals are at increased risk; homozygous PD individuals are at greater risk.

The present invention is based, in part, on the observation that a contributing mechanism for lead-induced neurological damage is that the metal causes reduced levels of arylsulfatase A (ASA) at critical stages of nervous system development. A genetic polymorphism in ASA that results in reduced cellular levels of the enzyme, and lead concentrations which cause a further reduction in the cellular activity of ASA lead to these abnormally reduced levels. The amount of enzymic activity, due to this compound effect, falls below a critical threshold level needed to maintain normal levels of sulfatide, the substrate for ASA. Experimental evidence supports this hypothesis. A relatively common polymorphism in the human gene coding for ASA has been identified which results in greatly reduced cellular levels of the enzyme. Furthermore, it has been demonstrated in vivo and in vitro, that lead is capable of causing a reduction in cellular ASA enzymic activity. Individuals with this genetic abnormality of ASA may be predisposed to lead-induced neuropathology. A relatively common polymorphism in the human ASA gene results in greatly reduced cellular levels of the enzyme. The frequency of the homozygous state for this polymorphism is three times greater in the African-American than Caucasian-American population.

In addition to the mutation resulting in absence of an N-linked glycan in ASA, a second mutation in the polyadenylation signal site of ASA results in greatly decreased expression of the enzyme. This mutation has been found to occur in tight linkage with the mutation that results in absence of the N-linked glycan. However, the N-glycoyslation site mutation may occur in the absence of the polyadenylation signal sequence mutation.

Identification and counselling of these individuals would be valuable in order to limit the incidence of neurotoxicity, e.g., lead toxicity. The present invention advantageously addresses a longstanding need to identify the genetic components of neurotoxicity, both to provide for testing that may help to prevent the onset of the condition or characterize the basis of neurotoxicity in an individual.

As used herein, a mutation in a residue 350 N-glycosylation site of at least one allele of ASA refers to an adenosine to guanosine transition at the nucleotide corresponding to position 1049 of the ASA cDNA. This mutation creates a new BsrI restriction endonuclease site in the mutant ASA gene.

As used herein, a mutation in a polyadenylation signal sequence of at least one allele of ASA refers to an adenosine to guanosine transition at the nucleotide corresponding to position 1620 of the ASA cDNA. This mutation creates a new MaeIII restriction endonuclease site in the mutant ASA gene.

As used herein, the term "neurotoxicity" refers to a disease or disorder characterized by reduced cellular levels of ASA activity to below threshold levels necessary for cellular sulfatide catabolism. Individuals with reduced ASA activity are found to be predisposed to toxicant-induced neuropathology, i.e., neurotoxicity.

As used herein, the term "toxicant" refers to a chemical moiety that adversely affects the cellular activity levels of ASA, or causes increased cellular levels of sulfatide. Physiologically, a toxicant may suppress ASA activity below levels required for effective sulfatide metabolism, or cause increased levels of sulfatide biosynthesis, or both. Examples of toxicants include lead, tricyclic antidepressants, and alcohol.

The invention relates to identifying individuals who are more susceptible to the pathological effects of toxicants. Although not intending to be limited to any particular theory or hypothesis, it is presently believed that the pseudodeficient (PD) mutation of ASA may contribute to adverse effects of toxicants in some individuals.

The term "pseudodeficiency (PD) mutation" as used herein refers to a mutation a gene such as the ASA gene of interest herein, that reduces the activity of that gene. The term "pseudodeficiency (PD) phenotype" refers herein to reduced levels e.g. ot ASA enzymatic activity as compared to normal levels, caused by the presence of one or more mutations in one or both alleles of the ASA gene. Additional description of "PD phenotype" is set forth hereinabove, at page 2, lines 4–12.

As used herein, the term "susceptible to neurotoxicity" refers to an increased likelihood of neurotoxicity relative to the general population; the term "susceptible to the pathological effects of toxicants" refers to an increased inability to properly metabolize the toxicants, or to increased damage in particular to the nervous system, from ingestion of the toxicant, than is seen on average in normal subjects. The marker of the present invention is not all inclusive; some individuals who suffer from a condition of neurotoxicity may lack the marker. Also, the marker is highly indicative, but not absolute: a few individuals homozygous for the PD-ASA allele may not be diagnosed as having a neuropathological condition. (This observation, however does not exclude the possibility that these "false-positive" individuals have a predisposition toward neurotoxicity, but simply have not yet developed the condition.)

The present invention is based on various observations. The electrophoretic variants of ASA are products of mutant ASA genes and certain of these mutant genes contain polymorphic sequences which are found in PD-ASA and cause reduced levels of cellular ASA. The PD-ASA mutation which causes loss of the N-glycosylation site accounts for a four-fold reduction in cellular levels of ASA due to a four- to five-fold decrease in the half-life of the enzyme. In addition, the PD-ASA mutation which results in the loss of the polyadenylation signal sequence causes a two-fold reduction in cellular ASA enzyme levels due to an approximately 50% reduction in expression of the enzyme protein. Previous work has shown that individuals who possess the PD-ASA polymorphism of the N-glycosylation site are 10–12 times more likely to be found in a population of male patients hospitalized or alcoholism and diagnosed with neuropsychiatric abnormalities than in the normal male population. The N-glycosylation site and polyadenylation signal polymorphisms of PD-ASA can be conveniently analyzed from DNA, obtained from buccal swabs, using a novel non-radioactive procedure employing restriction endonucleases and amplified genomic regions derived from unique primers in a PCR reaction.

The results and conclusions from this research led to the hypothesis that individuals expressing the polymorphisms of PD-ASA may be more susceptible to pathological consequences of exogenous toxicants and be at risk for developing psychiatric and neurological symptoms often associated with neurotoxicity. The paradigm for this condition is alcoholism, as related above. The results described in the Examples, infra, have unexpectedly permitted an expansion of this hypothesis to include the impact of environmental toxicants other than ethanol, such as lead, which may have a detrimental affect on individuals due to their direct or indirect action on ASA or sulfatide levels. Based upon this work, the implication of our hypothesis is that PD-ASA is principally an inherited abnormal glycosylation condition which is not benign, but rather causes an individual to be hypersusceptible to certain toxicants.

Accordingly, this invention relates to tests which identify individuals who are genetically hypersusceptible to neurotoxicity, e.g., from lead, tricyclic antidepressants, etc. In its broadest application, the invention identifies individuals who may exhibit a genetic predisposition to neurological damage caused by a number of diverse environmental/occupational toxicants as well as the side effects caused by certain pharmaceuticals. The present invention provides methods and kits for detecting the presence of the mutations that are indicative of a predisposition to detrimental effects of certain environmental/occupational neurotoxicants or side effects of certain pharmaceuticals. The tests are based upon the detection of a genetic polymorphism of an enzyme which causes the enzyme to be reduced to levels of 20–30% of that found in normal subjects. Greatly reduced levels of this enzyme are known to cause abnormal neurobehavioral activity in affected individuals. Lead and other toxicants as well as certain pharmaceuticals cause a reduction of this enzyme. Individuals with the genetic polymorphism detected by this invention and which causes reduced levels of the enzyme, may be hypersusceptible to these toxicants and pharmaceuticals since these persons possess threshold levels of the important enzyme. Enzyme levels below this threshold limit are associated with neurological damage.

The genetic abnormality associated with the greatest hypersusceptibility to neurotoxicants, homozygosity for the pseudodeficiency mutation of ASA, is detected in approximately 5% of the Caucasian and 15% of the African-derived populations in the United States, and is found in approximately 300 million people worldwide. Moreover, many more are heterozygous for this mutation. As shown infra, heterozygous pseudodeficient subjects have decreased ASA activity relative to normals. Since the effects of the neurotoxicants is to suppress ASA activity or increase the levels of cellular sulfatide, or both, according to the discoveries underlying the present invention, individuals who are heterozygous PD/normal are also expected to be more susceptible to neurotoxicity to toxicants than normals, although less so than homozygous PD-ASA. That is, the gene effect is dose related.

Previously, research led to the hypothesis that ingested ethanol directly or indirectly affects sulfatide metabolism by decreasing arylsulfatase A (ASA) levels and/or increasing sulfatide production. This interaction is expected to be of greater physiological significance with individuals possessing reduced ASA activity. Consequently, individuals expressing the genetic polymorphisms of ASA causing reduced levels of ASA may be more susceptible to the pathological consequences of exogenous ethanol and be at risk for developing psychiatric and neurological symptoms often associated with alcoholism.

Another implication of the invention is the association of the pseudodeficient ASA variants and endogenous depression. This association may relate to the response of patients to antidepressant medication. Tricyclic antidepressants such as imipramine are known to be lysosomotropic, resulting in the accumulation of lipids. Individuals in whom ASA, a lysosomal lipid-degrading enzyme, is compromised by mutation may be particularly prone to the side effects of lysosomotropic drugs. It is perhaps noteworthy that two patients with a unique variant of ASA (which included the Asn→Ser classical PD mutation, and an A→G transversion at nucleotide 2723. which eliminates the poly-A signal sequence of the mRNA, another classical PD mutation; a Thr→Ser conversion at amino acid 391 that is unlikely to have any major effect; and a G→T transversion, at nucleotide 842, changing tryptophan at residue 193 to cysteine, which is likely to dramatically affect ASA function) were being treated with monoamine oxidase (MAO) inhibitors and had been unresponsive to tricyclic antidepressants. Tricyclic antidepressants may be contraindicated in subjects with ASA deficiency.

The present invention provides methods and kits for detecting the presence of the mutations that are indicative of a predisposition to neurotoxicity or the pathological effects of toxicants. The immunochemical analytical techniques of the invention are particularly useful for detecting ASA mutants that lack the N-linked glycosylation site at residue 350.

The invention further provides molecular biological techniques that can be used to detect the presence of both the N-glycosylation site mutation and the polyadenylation signal sequence mutation, and discriminate between individuals who may be homozyaous or heterozygous for these mutations. These techniques are much simpler and more sensitive than the biochemical techniques previously used to characterize the phenotype of the PD mutation of ASA.

Finally, traditional biochemical techniques indicative of differences between the natively glycosylated and mutant forms of ASA, e.g., denaturing polyacrylamide gel electrophoresis with detection by immunoblotting, can also be used to identify those individuals who carry the PD mutation that results in absence of an N-linked glycan.

The invention advantageously provides kits for detecting the PD mutation in ASA based on the immunochemical analytic techniques and molecular biological analytical techniques of the invention.

Immunochemical Analysis

An epitope characteristic of an N-glycosylation mutation. As discussed above, one of the mutations characteristic of pseudodeficiency of ASA results in substitution of a serine residue for an N-glycosylated asparagine residue in residue 350 of ASA. Consequently, the mutant ASA lacks one of the N-linked glycans characteristic of the native ASA protein.

According to the invention, mutant ASA lacking an N-linked glycan at position 350 has a unique antibody epitope that is not present on the native (normal) ASA molecule. An antibody specific for this epitope can be blocked from binding to native ASA by steric hindrance: the large glycan group present at this position of ASA in the native protein can prevent or significantly inhibit binding of an antibody specific for the non-glycosylated site.

Accordingly, the present invention advantageously provides antibodies specific for the non-glycosylated epitope, that do not cross react with the native ASA protein. Such antibodies are particularly advantageous, as immunochemical screening assays are fast and relatively easy to perform. As discussed in greater detail infra, the antibodies of the invention are particularly useful for preparing diagnostic test kits, that can be used in a physician's office as well as sophisticated diagnostic laboratory settings.

Methods for obtaining antibodies. According to the invention, a peptide having an amino acid sequence corresponding to ASA in the region of amino acid residue 350, in which amino acid residue 350 is serine (rather than an N-glycosylated asparagine as in the native molecule) may be used as an immunogen to generate antibodies that recognize ASA lacking this N-glycosylation site, i.e., the product of the mutant ASA PD allele. An antibody reactive with the non-glycosylated form of ASA, and not reactive with the glycosylated form of ASA, is termed herein an antibody specific for the ASA mutant epitope. Such antibodies include but are not limited to polyclonal, monoclonal, chimeric, single chain, Fab fragments, and an Fab expression library.

Various procedures known in the art may be used for the production of polyclonal antibodies to the mutant ASA epitope. For the production of antibody, various host animals can be immunized by injection with the peptide corresponding to the mutant ASA epitope including but not limited to rabbits, mice, rats, sheep, goats, etc. In a preferred embodiment, the peptide is conjugated to an immunogenic carrier, e.g., diphtheria toxoid, bovine serum albumin (BSA), or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monoclonal antibodies directed toward the mutant ASA epitope, any technique that provides for the production of antibody molecules by continuous cell lines in culture may be used (see, e.g., Harlow and Lane, *Antibodies: A Laboratory Manual*, Cold Spring Harbor Laboratory Press: Cold Spring Harbor, N.Y.). These include but are not limited to the hybridoma technique originally developed by Kohler and Milstein [*Nature* 256:495–497 (1975)], as well as the trioma technique, the human B-cell hybridoma technique (Kozbor et al., *Immunology Today* 4:72 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology (PCT/US90/02545). According to the invention, human antibodies may be used and can be obtained by using human hybridomas (Cote et al., *Proc. Natl. Acad. Sci. USA* 80:2026–2030 (1983)] or by transforming human B cells with EBV virus in vitro [Cole et al., 1985, in *Monoclonal Antibodies and Cancer Therapy*, Alan R. Liss, pp. 77–96].

According to the invention, techniques described for the production of single chain antibodies (U.S. Pat. No. 4,946.778) can be adapted to produce ASA mutant epitope-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for an ASA mutant peptide or mutant ASA itself.

Antibody fragments which contain the idiotype (antigen binding region) of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immnunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize the non-glycosylated form of ASA (mutant ASA), one may assay generated hybridomas for a product which binds to the immunogenic peptide corresponding to such epitope. (As is well known in the art, the immunogenic peptide should be provided free of the carrier molecule used in any immunization protocol. For example, if the peptide was conjugated to KLH, it may be conjugated to BSA, or used directly, in a screening assay.)

A polyclonal or monoclonal antibody that reacts with the mutant ASA, or with the peptide corresponding to the mutant ASA epitope, should be tested for cross reactivity with normal (N-glycosylated at residue 350) ASA. Preferably, an antibody of the invention will demonstrate at least 10-fold, more preferably 100-fold, and most preferably greater than 1000-fold, lower binding to the native ASA than mutant ASA. i.e., an antibody of the invention should not cross react significantly with wild type ASA. The difference in binding of antibody to a protein can be evaluated by comparing antibody binding titer, relative affinity, or calculated affinity constants. Preferably, the evaluation is based on antibody binding titer, which is an easily determined empirical value.

The foregoing antibodies can be used in methods known in the art relating to the localization and structure of ASA, e.g., for Western blotting, measuring levels thereof in appropriate biological samples, etc.

The antibodies can be used to detect mutant ASA in a biological sample from an individual. The biological sample can be a biological fluid, such as but not limited to blood, serum, plasma, interstitial fluid, urine, cerebrospinal fluid, and the like. Preferably, ASA is detected in serum or urine, which are both readily obtained.

Alternatively, ASA can be detected from cellular sources, such as, but not limited to, platelets and fibroblasts. For example, platelets or fibroblasts can be obtained from an individual and lysed, e.g., by freeze-thaw cycling, or treatment with a mild cytolytic detergent such as, but not limited to, TRITON X-100®, digitonin, NONIDET P (NP)-40®, saponin, and the like, or combinations thereof (see, e.g., International Patent Publication WO 92/08981, published May 29. 1992). In yet another embodiment, samples containing cells and body fluids can be used.

The biological samples can then be tested directly for the presence of mutant ASA using an appropriate strategy (e.g., ELISA or radioimmunoassay) and format (e.g., microwells, dipstick [e.g., as described in International Patent Publication WO 93/03367, published Feb. 18, 1993], etc.). Alternatively, proteins in the sample can be size separated, e.g., by polyacrylamide gel electrophoresis (PAGE), in the presence or not of sodium dodecyl sulfate, and the presence of mutant ASA detected by immunoblotting (Western blotting). Immunoblotting techniques are generally more effective with antibodies generated against a peptide corresponding to an epitope of a protein, and hence, are particularly suited to the present invention.

Immunochemical assays. To characterize whether an individual is homozygous for the PD alleles of ASA, heterozygous, or homozygous for normal ASA, an antibody assay of the invention contemplates comparing the amount of ASA bound by an antibody specific for the PD mutant ASA to the amount of ASA bound by an antibody that binds to all forms of ASA, such as a rabbit anti-ASA polyclonal antibody. If the quantity of ASA bound by the antibody specific for the mutant ASA is about the same as the quantity bound by the antibody reactive with all ASA, then the individual is homozygous for the PD alleles. If the amount of ASA bound by the mutant-specific antibody is about half the amount bound by the antibody reactive with all forms of ASA, then the individual is heterozygous. Finally, if the amount of ASA bound by the mutant-specific antibody is much less than the amount bound by the antibody reactive with all forms of ASA, then the individual is homozygous normal.

In a preferred embodiment, the immunoassay of the invention comprises detecting the amount of ASA bound by an antibody by detecting the enzyme activity of ASA itself. Since mutant ASA demonstrates about the same amount of enzyme activity as native ASA, the total amount of enzyme activity directly relates to the quantity of ASA bound by antibody. For example, the mutant-specific antibody and the antibody specific for all forms of ASA can be separately affixed to solid phase supports, e.g., wells of a microtiter plate, or a solid adsorbent. A biological sample can be contacted with the bound antibody. The amount of ASA that binds to the antibody can be directly detected using an assay for ASA enzymatic activity. In a specific embodiment, the colorimetric substrate p-nitrocatachol sulfate can be used to indicate the presence of ASA [see Manowitz et al., *Biol. Psychiat.* 16:1107–13 (1981)].

In another embodiment, a sandwich immunoassay format using ELISA detection can be used. Accordingly, a first antibody can be attached to a solid phase support, e.g., the wells of a microtiter plate. This first antibody can bind to (capture) ASA in the sample. A second labeled antibody can be used to detect the presence of ASA captured by the first antibody. Either of the first or second antibody (but not both) can be an antibody of the invention, i.e., specific for mutant ASA. The other antibody should bind both forms of ASA.

Alternatively, a competitive assay format can be used. Inhibition of binding of a labeled antibody specific for the mutant epitope of ASA to a peptide corresponding to the ASA mutant epitope (or vice versa) by sample is indicative of the presence of mutant ASA in the sample.

For example, a solid phase assay system may comprise the solid substrate with either bound antibody and labeled mutant ASA peptide or bound mutant ASA peptide and labeled antibody, in which the antibody is specific for the mutant ASA epitope. A sample to be assayed is then placed in contact with the bound and unbound reagents. A competitive reaction between the labeled material and any unlabeled mutant ASA in the sample will prevent the retention of a concentration dependent quantity of the former on the solid substrate, whereupon it can be precisely quantitatively identified, either by detecting an increase in the amount of the label in the liquid phase (unbound to the solid phase). or detecting a reduction in the amount of labeled reagent bound to the solid phase.

The foregoing explanations of particular assay systems are presented herein for purposes of illustration only, in fulfillment of the duty to present an enabling disclosure of the invention. It is to be understood that the present invention contemplates a variety of immunochemical assay protocols within its spirit and scope.

Molecular Biological Analysis

The mutations characteristic of ASA pseudodeficiency can be identified using molecular biological techniques. In particular, the mutation of adenosine to guanosine at the nucleotide corresponding to position 1049 in the cDNA sequence and the mutation of adenosine to guanosine at the nucleotide corresponding to position 1620 of the cDNA sequence can be detected using highly specific oligonucleotide probes, creation of unique restriction endonuclease sites, or combinations thereof. Any of the standard techniques in molecular biology for detecting such mutations, including Southern analysis, Northern analysis, and dot hybridization with specific oligonucleotide probes under conditions of relatively high temperature and hybridization stringency, and the powerful polymerase chain reaction-based analytical techniques, can be used according to the invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); DNA Cloning: A Practical Approach, Volumes I and II [D. N. Glover ed. (1985); *Oligonucleotide Synthesis* [M. J. Gait ed. (1984); *Nucleic Acid Hybridization* [B. D. Hames & S. J. Higgins eds. (1985)]; *Transcription Anti Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984)].

If appearing herein, the following terms shall have the definitions set out below.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA—DNA, DNA—RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along one of the strands. A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. According to the present invention, the highest stringency hybridization for the length of the oligonucleotide probe to be used is required since hybridization of the probes must differentially detect sequences with a single base mutation.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

A particular advantage of the present invention is that it can be performed with buccal cells, which are easily obtained using a non-invasive procedure. This greatly reduces the level of discomfort that an individual may suffer and avoids the need for phlebotomy, as well as eliminates the likelihood of infection that accompanies more invasive procedures.

In preferred aspects, genomic DNA or mRNA is amplified by PCR, and the amplified DNA is tested for the presence of the mutation. PCR amplification is well known in the art [Cameron et al., *Science* 257:383–387 (1992); Saksela et al., *Proc. Natl. Acad. Sci. USA* 91:1104–1108 (1994)]. For example, mRNA can be detected by reverse transcriptase-initiated PCR [see, e.g., Saksela et al., *J. Virol.* 67:7423–27 (1993)]. PCR can be carried out, e.g., by use of a Perkin-Elmer Cetus thermal cycler and Taq polymerase (Gene Amp™, Boehringer Mannheim). The amplified PCR products can be analyzed by immobilization on membranes and hybridization with specific oligonucleotide probes, or by treatment with specific endonucleases and analysis of the products by gel electrophoresis. Labeling of the cleaved PCR products can be accomplished by incorporation of radiolabeled nucleotides, endlabeling, e.g., with $\gamma^{32}$P-ATP, or by staining with ethidium bromide. The present invention provides specific preferred examples of PCR-based analysis of ASA mutations: one, in which genomic DNA (or mRNA) is amplified, and the presence of a restriction site unique to the mutant gene is determined; and a second, in which the genomic DNA (or mRNA) is amplified and the mutation detected by binding of specific oligonucleotide probes. DNA from any available source can be used for the PCR-based analysis. Sufficient DNA can be obtained from a finger-prick or from saliva-born buccal cells.

PCR amplification and detection of unique restriction endonuclease sites. The present invention provides primers for PCR amplification of a segment (preferably about 200 nucleotides in length) of genomic DNA corresponding to the ASA gene or a portion thereof containing the mutated nucleotide; or primers for reverse transcriptase-PCR of mRNA encoding the ASA gene; and a restriction endonuclease specific for a restriction site that is unique to either the mutant ASA gene (and is not found in the native ASA gene), or a restriction site that is unique to the native ASA gene (and is not found in the mutant ASA gene). Preferably, the primers for use according to the present invention are engineered or selected to incorporate an internal control endonuclease site corresponding to the site produced by the mutation. This way, amplified DNA will always contain an endonuclease site, so endonuclease enzyme activity can be detected even if the mutation that creates the endonuclease site of interest is not present.

It has been discovered that the mutation leading to replacement of $Asn_{350}$ with Ser results from an A to G transition, which creates a new BsrI restriction endonuclease site in the ASA gene. It has also been discovered that the mutation in the polyadenylation site resulting from an A to G transition creates a new MaeIII restriction endonuclease site in the ASA gene. By amplifying a portion of the ASA gene containing the mutated nucleotide, and subsequently treating the amplified product with the restriction endonuclease, the presence of the mutation can be determined by cleavage of the amplified DNA into new fragments that are not formed upon endonuclease treatment of DNA from the native ASA gene. These fragments can be detected readily simply by size on an agarose or polyacrylamide gel. The fragments can be labeled with radionucleotides during PCR amplification, or alternatively detected by ethidium bromide or silver staining. The presence of fragmented DNA indicates that the individual from whom the DNA was originally obtained is homozygous for the PD mutation of ASA; presence of fragmented DNA and unfragmented DNA indicates that the individual from whom the DNA was originally obtained is heterozygous for the PD mutation of ASA; and the presence of only unfragmented DNA indicates that individual from whom the DNA was originally obtained is homozygous for the normal ASA allele.

In a specific example, infra, the invention provides a 5' primer having the sequence TGATGGCGAACTGAGT-GACT (SEQ ID NO:9) and a 3' primer having the sequence AAGGATCTGGGATCAGGGGT (SEQ ID NO:10), to amplify about a 200 nucleotide region of the ASA gene in proximity to the mutation at the nucleotide corresponding to number 1049 of the cDNA sequence. As note above, the mutation at this site results in introduction of a BsrI endonuclease restriction site.

More preferably, a 5' primer CACCCCAACCTTGATG-GCGAACTGGGTGAC (SEQ ID NO:14) and a 3' primer AAGGATCTGGGATCAGGGGT (SEQ ID NO:10) are used. The 5' primer generates a 211 base pair fragment spanning the third potential N-glycosylation site at amino acid residue 350, but has been modified by substitution of a G for A so as to introduce a BsrI site 25 nucleotides from the 5' end, which acts as an internal positive control for BsrI enzyme activity. The presence of two BsrI restriction endonuclease sites is indicative of the mutation; the presence of only one site is indicative of wild type; and the presence of no BsrI site indicates that the experiment has not yielded a meaningful result. Alternatively, the invention provides a 5' primer having the sequence AGCTTGCTGCCATTGCCCA (SEQ ID NO: II) and a 3' primer having the sequence CATTACCCCAGGATTGGTCGAA (SEQ ID NO:12), which primers amplify an approximately 182 nucleotide fragment that contains the polyadenylation signal mutation at the nucleotide corresponding to number 1620 of the cDNA sequence. As noted above, the mutation at this site results in introduction of a MaeIII restriction site. Advantageously, this primer set incorporates a naturally occurring MaeIII site 29 nucleotides from the 3' end of the PCR product. This site serves as an internal positive control for restriction endonuclease activity.

Most preferably, both sets of primers and restriction endonucleases are used to detect either or both mutations in an ASA allele.

PCR amplification and hybridization of specific probes. In another embodiment, the invention provides primers for amplifying a segment of genomic DNA corresponding to the ASA gene or a portion thereof containing the mutated nucleotide; or primers for reverse transcriptase-PCR of mRNA encoding the ASA gene; and a labeled oligonucleotide probe for hybridizing to amplified DNA and detecting the presence of a mutation in the ASA gene at a position corresponding to nucleotide 1049 of the cDNA, or nucleotide 1620 of the cDNA, or both. In a specific embodiment, infra, the oligonucleotide probes AAGGTGACATTGGGCAGTGG (SEQ ID NO:5) (specific for the native ASA gene around the nucleotide corresponding to position 1049 of the cDNA) and AAGGTGACACTGGGCAGTGG (SEQ ID NO:6) (specific for the mutant ASA gene around the nucleotide corresponding to position 1049 of the cDNA) can be hybridized to the amplified sequence, wherein hybridization of the former probe at 55° C. with washing at 62° C. is indicative of a normal ASA allele, and hybridization of the latter probe at 55° C. with washing at 60° C. is indicative of a PD allele. Alternatively, the oligonucleotide probes CTGGTGTTATTACGTTATC (SEQ ID NO:7) (specific for the native ASA gene around the nucleotide corresponding to position 1620 of the cDNA) and CTGGTGTTACTACGTTATC (SEQ ID NO:8) (specific for the mutant ASA gene around the nucleotide corresponding to position 1620 of the cDNA) can be hybridized to the amplified sequence, wherein hybridization of the former probe at 48° C. with washing at 52° C. is indicative of a normal ASA allele, and hybridization of the latter probe at 48° C. with washing at 52° C. is indicative of a PD allele. These probes are full described in a reference by Gieselmann et al. [supra (1989)].

In another aspect, the invention provides for detection of the mutated nucleotides in PCR-amplified fragments of the ASA gene by immobilization of the amplified DNA on nitrocellulose or Nylon membranes, and hybridization with labeled oligonucleotide probes complementary to the normal or mutated sequence, a technique known as dot-hybridization analysis. The oligonucleotide probes could be radio-labeled (e.g., with $^{32}$P nucleotides) or non-radioactively labeled (e.g., with digoxygenin), in which case detection of hybridization is by an enzyme-linked color reaction, or, preferably, by chemiluminescence detection.

Biochemical Analysis

As noted above, absence of an N-linked glycan from mutant ASA results in detectable differences in biochemical characteristics related to the extent of glycosylation of the mutant ASA compared to native ASA. The most obvious difference is in electrophoretic mobility. In particular, PD mutant ASA has an apparent molecular weight of about 59 kD by PAGE, whereas normal ASA has an apparent molecular weight of 62 kD under identical electrophoretic conditions.

In another aspect, greater mobility difference is observed upon PAGE analysis between endo-N-acetlyglucosaminidase H (endo-H) treated mutant ASA and normal ASA. For example, a greater loss of mass is detected with ASA from a normal subject upon endo-H treatment (4 kD) than from ASA from a PD subject (1 kD). Such a difference in mass would not be expected in the absence of a difference in the extent of glycosylation between the mutant and normal forms of ASA.

Generally, any assay that can distinguish between native ASA, which contains two N-linked glycan moieties, and mutant ASA, which lacks one of the N-linked glycan moieties, can be used to identify individuals who are homozygous for PD mutant ASA. For example, an assay that directly measures the presence or quantity of N-linked glycans on a protein can be used to detect mutant ASA.

As with the immunoassays described above, the presence of normal ASA should be evaluated in the biochemical assays. If no normal ASA is detected, but only mutant ASA. then the individual is homozygous for the PD mutation. However, if both normal and mutant ASA are present in a sample, the individual is heterozygous, and if only normal ASA is detected, the individual is homozygous normal.

As with the immunoassays, biochemical assays can be used to detect mutant ASA in a biological sample from an individual. The biological sample can be a biological fluid, such as but not limited to, blood, serum, plasma, interstitial fluid, urine, cerebrospinal fluid, and the like. Preferably, ASA is detected in serum or urine, which are both readily obtained. Alternatively, ASA can be detected from cellular sources, such as, but not limited to, platelets and fibroblasts. Platelets or fibroblasts can be obtained from an individual and lysed, e.g., by freeze-thaw cycling, or treatment with a mild cytolytic detergent such as, but not limited to, TRITON X-100®, digitonin, NP-40, saponin, and the like, or combinations thereof (see, e.g., International Patent Publication WO 92/08981, published May 29, 1992). The cellular lysates can then be assayed directly, with detection of ASA bands by an ASA-specific calorimetric enzyme assay on native (non-denaturing) PAGE, or by Western analysis of proteins separated by SDS-PAGE. Alternatively, ASA in the sample can be enriched by affinity purification or immunoadsorption of ASA present in the sample, followed by PAGE with detection of total protein, ASA enzyme activity, or immunoblotting. Chemical analysis for the presence of N-linked glycans can also be used to determine the biochemical characteristics of ASA in the sample after affinity purification or immunoadsorption.

Kits

The present invention advantageously provides specific kits for use in locations ranging from a physician's office to a sophisticated medical laboratory. The kits of the invention provide reagents necessary to determine whether an individual is homozygous for the PD mutation of ASA, and thus, to evaluate whether the person may be susceptible to neurotoxicity.

The kits of the invention fall into two categories: kits for immunoassays to detect the presence of mutant ASA; and kits to detect mutations in the genomic DNA or mRNA encoding ASA.

Immunoassay test kits. An immunoassay test kit may be prepared for the demonstration of mutant ASA in a sample, comprising:

(a) an antibody specific for the mutant epitope of ASA, as described above;

(b) an antibody specific for all forms of ASA; and (c) means for quantitating binding of the antibody specific for the mutant epitope and the antibody specific for all forms of ASA to ASA in a sample from an individual.

The means for detecting binding of the antibody to mutant ASA in a sample from an individual can comprise any of the immunoassay strategies and formats described above.

In a preferred aspect of the invention, the antibody specific for the ASA mutant epitope is a monoclonal antibody generated in mice against the peptide Ac-Cys-Ala-Pro-Leu-Pro-Ser-Val-Thr-Leu-Asp-Gly-Phe-Asp-NH$_2$ (SEQ ID NO:13).

In addition to an antibody and means for detecting binding of antibody to mutant ASA in a sample, an immunoassay kit of the invention may further comprise other reagents and, optionally, directions for use of said kit.

Kits to detect mutations in the genomic DNA or mRNA encoding ASA. In another embodiment, the invention provides test kits for detecting the presence of a PD mutation in the ASA alleles in an individual. In one embodiment, the kit provides for detecting the mutation in the codon encoding asparagine, which after an A to G mutation encodes serine in the mutant ASA. In another embodiment, the kit provides for detecting the mutation in the polyadenylation signal of the ASA gene. In a preferred embodiment, a test kit of the invention provides for detecting both mutations.

Accordingly, a test kit of the invention may comprise:

(a) primers for amplifying a segment of genomic DNA corresponding to the ASA gene or a portion thereof containing the mutated nucleotide; or primers for reverse transcriptase-PCR of mRNA encoding the ASA gene;

(b) a labeled oligonucleotide probe for hybridizing to amplified DNA and detecting the presence of a mutation in the ASA gene at a position corresponding to nucleotide 1049 of the cDNA, or nucleotide 1620 of the cDNA, or both.

Such a kit may further comprise instructions relating to the appropriate hybridization conditions and temperature: hybridization solution (in lyophilized, concentrated, or correct strength) for use in hybridizations; a membrane for blotting the amplified DNA: reagents for labeling the oligonucleotide probes (e.g., $^{32}$P-labeled nucleotides or digoxygenin); and other reagents.

In another embodiment, a kit of the invention comprises (a) primers for PCR amplification of a segment (preferably about 200 nucleotides in length) of genomic DNA corresponding to the ASA gene or a portion thereof containing the mutated nucleotide; or primers for reverse transcriptase-PCR of mRNA encoding the ASA gene;

(b) a restriction endonuclease specific for a restriction site that is unique to either the mutant ASA gene (and is not found in the native ASA gene), or a restriction site that is unique to the native ASA gene (and is not found in the mutant ASA gene).

In a preferred embodiment, primers are engineered or selected to incorporate a second endonuclease site corresponding to the endonuclease site created by the mutation, which second endonuclease site acts as a positive control for endonuclease enzyme activity. Preferably, such a kit incorporates the primers and restriction endonucleases specifically disclosed above, and exemplified in Examples 2 and, more preferably, 3, infra. Such a kit may further comprise instructions relating to the appropriate amplification conditions and endonuclease cleavage conditions; gels for electrophoresis of the PCR products; and other reagents. Optionally, the kit may provide reagents for detecting the amplified DNA, e.g., ethidium bromide, or a labelled nucleotide triphosphate (e.g., $^{32}$P-thymidine-, adenosine-, or cytosine-triphosphates) for incorporation in the amplified DNA.

Model Test Systems

In order to test the validity of correlates one and two, an animal model which represents the biochemistry and physiology of the human with high fidelity is desirable. Though such models are used extensively to study a number of pathological conditions, a rodent model, capable of reflecting a reduced ASA human has not yet been developed. Nevertheless, Fujita et al. (1995) recently was able to develop a total saposin knockout mouse which, when homozygous, displayed many of the symptoms of the analogous human demyelination conditions and of other rodent myelin mutants. Furthermore, the observation by Santra et al. (1989) of a lead-induced reduction of ASA in rats is important to the proposal reported here and should be extended by us. In addition, lead may impact sulfatide metabolism, not only by decreasing ASA levels, but also by causing changes in the biosynthesis of sulfatide or its immediate precursor, galactosyl ceramide, by influencing the intracellular cellular activity of galactosylceramide sulfotransferase (CST) or UDP-galactose:ceramide galactosyltransferase (GT), respectively. CST is best studied in oligodendrocytes. Human fibroblasts, in particular, lack significant expression of this enzyme. Accordingly, the examination and use of CNS tissue to study the impact of lead is best done on small animals such as rodents. For example, the effect of lead on the cellular activity of central nervous system CST, GT, and ASA, as well as tissue concentrations of sulfatide and galactosyl and lactosyl ceramide in new born rats who have been exposed to lead in utero and subsequently through maternal milk from exposed mothers can be evaluated. In addition, the effect of lead on the cellular activity of CST, GT and ASA in vitro cultured oligodendrocytes exposed to lead in the culture medium can be examined.

In vivo studies with rats. Sixty Long-Evans female rats are bred as described by Widzowski and Cory-Slechta [*Neurotoxicology* 15:295–308 (1994)]. At one week of gestation, the pregnant rats are placed on a diet of Purina Test Diet's semipurified diet and water containing lead acetate at a concentration of 0, 100, 300, 900 or 2000 ppm (Widzowski and Cory-Slechta, supra; Cory-Slechta, *Neurotoxicology* 16:83–96 (1995)]. After the third week of gestation, each pregnant rat is placed in an individual cage and exposed to the same regimen. Following birth, the pups are allowed to receive milk from the exposed mother. Five pups from each group are sacrificed by decapitation at 1, 2, 4 and 8 weeks of age. Following the protocol of van der Pal et al. [*Biochem. Biophys. Acta* 1043:91–96 (1990)] brain, spinal cord, and liver are removed from each sacrificed animal. Tissue homogenates are prepared to perform enzyme and protein analysis and for determination of total tissue content of galactosyl and lactosyl ceramides and sulfatides. ASA is measured by the method of Baum et al. [*Clin. Chem. Acta* 4:453–455 (1959)] and protein by the method of Lowry et al. [*J. Biol. Chem.* 193:262–275 (1951)]. GT is analyzed by the method of Neskovic et al. [*J. Neurochem.* 47:1412–1418 (1986)], CST by the method of van der Pal et al. (supra), and individual glycolipids by the method of Vos et al. [Biochem. Biophys. Acta 1211:125–149 (1994)]. All enzyme, lipid, and protein assays are performed in quintuplicate. Blood lead concentrations are determined by atomic absorption spectroscopy (Markowitz and Rosen, *J. Pediatr.* 119:305–310) on blood obtained from tail veins of mothers at various times during the course of treatment, and from heart bleeding of pups at the time of sacrifice.

Mean, s.e.m., and range of values are used to describe each parameter. For enzyme specific activities and lipid concentrations from brain, spinal cord, or liver, the effect of time and presence of lead in the food source is analyzed by a two-way analysis of variance. For those showing significant effects, a post hoc Tukey test is done at each time point. A significance level of 0.05 is used for this and all other statistical tests.

In vitro tissue culture studies with rat cells. Highly enriched cultures of oligodendrocytes are obtained from newborn rat brain as described by Fressinaud et al. [*J. Cell. Physiol.* 141:667–674 (1989)]. After two days in vitro, the culture medium is exchanged with medium containing lead acetate (0.5, 26, 20 and 100 $\mu$M). Control cultures are maintained in parallel without added lead acetate. At varying times up to 30 days in vitro, select cultures of oligodendrocytes are collected and washed. The oligodendrocytes are analyzed for GT as described by Neskovic et al. [*J. Neurochem.* 47:1412–1418 (1986)] and CST as detailed by van der Pal et al. (supra). ASA is measured by the procedure of Baum et al. (supra) and protein by the method of Lowry et al. (supra). All enzyme and protein assays are performed in quintuplicate. For long term culture experiments, fresh medium containing lead acetate, where appropriate, is added periodically to replace a portion of the conditioned growth medium. Averages, means, s.e.m. and range of values are determined for each measured quantity. A one-way analysis of variance are performed with lead acetate dosage as the independent variable and enzyme specific activities as the dependent variable. Post-hoc comparisons of the values at different concentrations of lead are performed using the Tukey Test. To determine whether a lead acetate effect is similar across different enzymes, a two-way analysis of variance are employed. The enzyme specific activities are calculated relative to their values at zero lead concentration. The effects of lead acetate dosage, enzyme specific activities, and the interaction between lead concentration and enzyme specific activities are explored.

Experiments employing human skin fibroblasts. Experiments designed to explore correlate number three are based upon the sulfatide loading test developed for the diagnosis of MLD using in vitro cultured human fibroblasts. It is now well established that the sulfatide loading test employing fibroblasts, derived from skin biopsy, correlates with the ability of the individual to desulfate normal steady-state levels of sulfatide, thereby influencing cellular and systemic levels of this glycolipid. Fibroblasts of patients exhibiting symptoms of MLD and having elevated urinary sulfatide levels exhibit a reduced ability to catabolize sulfatide by this test. Individuals who have normal levels of ASA or residual amounts of the enzyme above a critical threshold level, and who do not have elevated concentrations of urinary sulfatide, exhibit normal catabolism of sulfatide by this test. Interestingly, in rare instances, a few individuals who present with late-onset atypical MLD and urinary sulfatide values much lower than those for usual MLD patients, but higher than control subjects, donate fibroblasts which exhibit normal sulfatide loading values [Naidu, In *The MRI Suggests a Leukodystrophy, But Tests Are Negative. What Should We Do?*, J. M. Trager, Ed., United Leukodystrophy Foundation, Inc.: Sycamore, Ill., p. 38 (1995)]. Only when the cells of these persons are stressed in in vitro cell culture by the addition of HEPES to the culture medium, do the ASA levels of these persons become slightly more reduced, resulting in these fibroblasts yielding sulfatide loading values consistent with the MLD diagnosis of the individual. Fibroblasts of unaffected persons stressed in a similar manner maintain a normal sulfatide loading value. Though the molecular basis of this HEPES effect is not known, it is believed due to a direct lysosomotropic effect of this weak base causing reduced ASA levels in the fibroblasts [Fluharty, in *The MRI Suggests a Leukodystrophy, But Tests are Negative. What Should We Do?*, Ed. J. M. Trager, United Leukodystrophy Foundation, Inc., Sycamore, Ill., p. 38 (1995)]. Though probably caused by different mechanisms, the effect of lead on cellular levels of ASA may be analogous to that of HEPES. As reported in the Examples, 5–20 $\mu$M lead acetate, added to the culture medium of normal fibroblasts, causes a 32–36% reduction of cellular ASA activity. The effect of lead on sulfatide catabolism is expected to be greater on cells from individuals who have an hereditary form of reduced residual ASA activity than on cells from people who exhibit normal steady-state levels of ASA activity. Accordingly, the sulfatide loading test is productively used as a measure of the impact of lead on sulfatide metabolism in cells possessing different polymorphisms associated with the N-glycosylation site and polyadenylation signal site sequences of pseudodeficient ASA.

Fibroblasts serve as a good system to study the effect of lead on ASA catabolism in human cells which are isolated from individuals with different genetic polymorphisms of the ASA gene. Though these cells lack the ability to synthesize sulfatide, they do contain representative amounts of ASA and are a convenient source of cells, for laboratory propagation and experimentation, which can be obtained from human donors. A collection of skin biopsy-derived fibroblast cultures from individuals possessing the different PD-ASA associated polymorphisms, as well as a considerable number of cultures from persons with normal ASA alleles can be used. Such fibroblasts are genotyped with respect to ASA polymorphisms and many have been analyzed in regard to their ASA enzymic levels when grown in culture with normal medium. Select fibroblast cultures possessing different allele combinations of the normal gene, an MLD gene, or the gene exhibiting one or both PD-ASA associated polymorphisms, thereby yielding cells containing different levels of residual ASA activity, are grown in normal medium as described infra, as well as in medium containing 0.5, 5 and 20 $\mu$M lead acetate as detailed above (see Examples). Cells that carry an MLD gene are included as reference controls. ASA is measured by the procedure of Baum et al. (supra) and sulfatide loading tests are performed as described by Kudoh and Wenger [*J. Clin. Invest.* 70:89–97 (1982)]. Precautions as detailed by Leinekugel et al. [*Hum. Genet.* 88:513–523 (1992)] are taken to insure that the description of the consequence of the conditions used in the in vitro assay, is indicative of those for the in vivo whole human organism.

Descriptive statistics (means, s.e.m., range of values) are calculated for the enzyme specific activity and rate of sulfatide degradation at each lead acetate concentration. A one-way analysis of variance is used to determine if there is a lead acetate dosage effect for each parameter measured.

The genotype of the cells that may be studied are shown in the following table. The sequence including nucleotide residue 1788 encodes for an N-glycosylation site. The normal enzyme contains residue 1788A and the polymorphism associated with PD is residue 1788G. This nucleotide change results in a change in the amino acid sequence causing loss of the N-glycosylation site. The normal sequence at the polyadenylation recognition site contains nucleotide residue 2723A as opposed to residue 2723G found in PD-ASA.

| Sequence Polymorphism | Description |
|---|---|
| 1. 1788A, 2723A/1788A, 2723A | Normal homozygote |
| 2. 1788G, 2723A/1788G, 2723A | N-glycosylation PD-ASA homozygote |
| 3. 1788G, 2723G/1788G, 2723G | Double PD-ASA mutation homozygote |
| 4. 1788G, 2723A/1788A, 2723A | N-glycosylation PD-ASA/normal heterozygote |
| 5. 1788G, 2723G/1788A, 2723A | Double PD-ASA mutation/normal heterozygote |
| 6. 1788G, 2723G/1788G, 2723A | Double PD-ASA mutation/N-gylcosylation PD-ASA heterozygote |
| 7. MLD/MLD | MLD homozygote |
| 8. MLD/1788A, 2723A | MLD/normal heterozygote |
| 9. MLD/1788G, 2723G | MLD/double PD-ASA mutation heterozygote |

To further understand the mechanism by which exposure of fibroblasts to lead results in decreased cellular levels of ASA activity, two possibilities can be investigated. These are: 1) That lead causes a decrease in the amount of ASA molecules in the cell without changing the specific enzymic activity of the ASA, such as by inhibiting its synthesis: and 2) that lead either directly or indirectly causes inactivation or inhibition of the ASA without altering the total steady-state level of the amount of ASA molecules in the cell. Both possibilities, as well as the possible combination of both mechanisms, are tested by employing the following biochemical experiments. Normal and PD-ASA fibroblasts are grown in media containing or lacking lead acetate as described in Preliminary Results. Both total cellular ASA enzymic activity (per mg total cellular protein) as presented above, as well as the amount of specific cellular ASA protein is determined. The amount of ASA protein in a measured amount of total cellular protein is found employing a monospecific rabbit anti-ASA serum and the technique of quantitative immunoblotting.

In addition, it will be determined if lead alters the normal subcellular localization of ASA. Lead may cause the cell to segregate lysosomal enzymes abnormally, resulting in the secretion or abnormal compartmentalization of ASA. To accomplish this, quantitative biochemical subfractionation procedures as described by Gorman and Porctz (supra) on normal and PD-ASA fibroblasts grown in medium either lacking or containing lead acetate as described above are performed. ASA, other lysosomal hydrolases, and various markers denoting specific subcellular compartments, as well as protein are analyzed in this experiment. Experiments are performed repeatedly and presented as described by Gorman and Poretz (supra).

Clinical association studies with children. A clinical subject cohort will be employed in a longitudinal study concerned with the cognitive effects of lead toxicity in children [Ruff et al., *JAMA* 269:1641–1646 (1993); *Environ. Health Perspect.* (1996)]. The combined studies represent approximately 215 children enrolled on the basis of blood lead levels of 25 to 55 µg/dl and with erythrocyte protoporphyrin levels greater than 0.65 mg/L. Cognitive function was determined by the Bayley Scales of Mental Development or Stanford-Binet Intelligence Scale for children of the appropriate age groups and where appropriate, modified estimated scores were used. The children in the cohort were predominantly African-American (ca. 37%), or Hispanic (ca. 58%) and approximately 57% were boys. A set of background variables served as covariates in the earlier study (see Ruff et al., supra 1993) and included factors of age, sex birth order, socioeconomic status, health and language.

In order to obtain DNA samples from individual children in the cohort, parents, or guardians of the children are contacted and encouraged to visit the center so that the children can donate cells and cellular debris obtained by buccal swab with a cytology brush [Richards et al., *Hum. Molec. Genet.* 2:159–163 (1993)]. The buccal swab, performed by a trained professional personnel, is non-invasive and performed without causing discomfort or risk to the child. The buccal smears are collected for ASA genotyping. The samples are coded, and the relationship of each coded sample to the code identifying the cognitive and lead-load characteristics of the donor is kept from those responsible for the genotyping until after the genotyping of the individual sample is complete. All tests use code numbers and not subject names. The personal identities of the donors are kept in secure files. DNA is extracted with NaOH as described by Richards et al. (supra). Polymerase chain reaction (PCR) amplification of the regions of the ASA gene of concern, and analysis of the nature of the polymorphic sites are performed.

In addition, residual blood obtained for lead measurements from 800 children participating in a multi-center randomized trial of chelation therapy can be tested. Each child is monitored regularly for blood lead levels and evaluated initially by the Bayley Scales of Infant Development II and three years later with the Wechsler Preschool and Primary Scales of Intelligence—Revised. Blood is used as a source of DNA in order to genotype each child for the N-PD polymorphism denoting inherited reduced levels of ASA so that interactions and main effects with blood lead and cognitive test results can be evaluated.

Cells from blood previously taken for lead determination are sent for ASA genotyping. The samples are coded, and those responsible for performing and interpreting the genotyping are blind to the code identifying the cognitive and lead-load characteristics of the donor until after the genotyping of samples is complete. All tests use code numbers and not subject names. The personal identities of the donors are kept in secure files. The genotyping is performed by procedures described above infra for the analysis of such polymorphic sequences in the ASA gene [Ricketts et al, *Neuropsych. Genet* (1995)]. DNA is extracted with NaOH. Polymerase chain reaction (PCR) amplification of the regions of the ASA gene of concern, and analysis of the nature of the polymorphic sites are performed.

(i) The N-glycosylation site mutation which corresponds to a change of an asparagine to serine (N350S)

Oligonucleotide primers for PCR amplification have been designed with the aid of the MacVector program (Eastman Kodak) and obtained from National Biosciences (Plymouth, Minn.). A 200 base pair fragment spanning the third potential N-glycosylation site at amino acid residue 350 (cDNA nucleotide 1049) is amplified with the primers ASA2c (5'-TGATGGCGAACTGAGTGACT) and ASA4nc (5'-AAGGATCTGGGA-TCAGGGGT) using about 0.5 µg of DNA in 50 mM KCl, 10 mM Tris (pH 8.3), 1.5 mM $MgCl_2$, 200 µM each of dATP, dTTP, dCTP, and dGTP and 1.25 units of Taq DNA polymerase. Following an initial denaturation at 95° C. for 3 minutes, amplification is carried out for 35 cycles by denaturation at 95° C. for 30 seconds, annealing at 56° C. for 1 minute and extension at 72° for 30 seconds in a 50 µL volume using an MJ Research PTC100 thermal cycler.

Following PCR amplification, the reaction is sequentially extracted with an equal volume of phenol and chloroform, and the DNA is ethanol precipitated in the presence of 0.3 M sodium acetate. Following a 70% ethanol wash, the pellet is dried and dissolved in 20 μl of 0.1 mM EDTA, 1 mM Tris (pH 8.0). An aliquot (6 μl) of the DNA is digested in a final volume of 25 μl with 10 units BsrI, the restriction endonuclease, in the buffer provided by the supplier (New England Biolabs) at 65° C. for 3 hours. The 200 base pair fragment is cleaved by BsrI if the N-glycosylation site is mutated, resulting in two fragments of 112 and 88 base pairs.

(ii) The polyadenylation signal site mutation

A 182 base pair fragment spanning the polyadenylation signal site at cDNA nucleotide 1620 is amplified with primers ASA3c (5'-AGCTTGCTGCCATTGCCCA) and ASA5nc (5'- CATTACCCCAGGATTGGTCGAA) using the same conditions described above for the ASA2c/ASA4nc primer pair except that the amplification is achieved using a rapid two step cycling program (94° C. for 20 seconds, and 56° C. for 30 seconds for 35 cycles).

A volume of 9.8 μl is digested with 2 units MaeIII in a final volume of 12 μL at 55° C. for 3 hours. In the absence of a mutation the 182 base pair fragment is cleaved to fragments of 153 and 29 nucleotides. When the polyadenylation signal sequence is mutated, the 153 base pair fragment is further cleaved to 129 and 24 base pair fragments.

All PCR and restriction enzyme digestion products are separated by electrophoresis through 7.5% polyacrylamide gels run in TBE buffer (Ausubel et al., *Current Protocols in Molecular Biology*, John Wiley & Sons, Baltimore, Md. (1994)] and photographed after staining with ethidium bromide.

To determine if the N-glycosylation site polymorphism of PD-ASA is related to cognitive performance (as measured by the cognitive index—CI), several statistical tests are conducted. First, the population is divided into two groups, those who are PD/PD homozygous and those who are not PD/PD homozygous; or alternatively into three groups, those who are PD/PD homozygous, or PD/N heterozygous, or N/N homozygous. The CI between the two groups or among the three groups are compared using an analysis of covariance, with PD-genotype as the independent variable and the blood-lead level as a covariate. A test confirming the homogeneity of slope of the CI with respect to the blood-lead level across groups is also conducted. Another approach which is considered is to use a regression model with CI as the dependent variable and the genotype and blood-lead level as independent variables. The significance of the genotype coefficient in the regression equation is of primary interest.

Though the frequency of the PD polymorphisms in the Hispanic population is not known, the data for the Spanish [Chabas et al., *Clin. Genet.* 44:320–323 (1993)] and the Cheyenne Indian populations [Ricketts et al., supra, 1995] suggest that we can expect frequencies greater than seen in the total Caucasian-American population. Given the relatively high frequency of the N-glycosylation site polymorphism of PD in the African-American population, and the high percentage of African-Americans in the cohort being studied, the number of subjects that is necessary to obtain statistically significant results is considerably smaller than that needed for examining a group with a profile representative of the U.S. population at large.

The invention may be more completely understood by reference to the following on-limiting examples, which are provided solely as an example of a specific embodiment of the invention and not by way of limitation thereof.

EXAMPLE 1

The Association of Lead Toxicity with Pseudodeficiency of Human Arylsulfatase A

This Example concerns the discovery that genetic variants of arylsulfatase A (EC 3.1.6.8) are more prevalent in lead toxicity susceptible individuals. These variant enzymes possess the pseudodeficient $Asn_{350}$-Ser mutation of arylsulfatase A and, consequently, lack an N-linked glycan unit. Individuals expressing these genetically determined variants of arylsulfatase A show reduced enzymic activity and intracellular half-life. The consequence of this interaction would be to cause neuropathological symptoms common to metachromatic leukodystrophy patients and some alcoholic individuals, and/or influence the toxicity pathway of lead by impacting on sulfatide-associated neurotransmitter systems.

Methods and Results

The starting point for this work was the sulfatide loading test, which provides a more accurate measure of the cells' ability to catabolize sulfatide than direct measurement of ASA activity in a water soluble cell extract assay. Fibroblasts from an MLD patient, when examined with this test, demonstrate a great inability to desulfate the incorporated sulfatide. As shown in FIG. 1, the accumulated evidence [Kappler el al., *Hum. Genet.* 86:463–470 (1991); Conzelmann and Sandhoff, *Dev. Neurosci.* 6:58–71 (1991); Leinekugel et al., *Hum. Genet.* 88:513–523 (1992)] comparing the results from the sulfatide loading test and measurements of total ASA activity in cellular lysates by use of a water soluble substrate, demonstrates that normal cells apparently contain a 4–5 fold excess of ASA needed to maintain normal levels of sulfatide. MLD patients who possess 0–5% the ASA activity of normal subjects (as measured by a synthetic substrate), and exhibit 2–50% the normal ability to degrade sulfatides as determined by the sulfatide loading test (see FIG. 1. MLD-late infantile and MLD-adult-late onset). Individuals who are homozygous for PD-ASA show a reduced ASA activity of 10–30% of normal, but demonstrate a normal sulfatide loading profile (FIG. 1, PD/PD). Those persons who are heterozygous for MLD and PD-ASA (FIG. 1, MLD/PD), however, show levels of enzymic activity 5–10% that of normal and exhibit a reduced sulfatide catabolism equivalent to 15–75% of that by homozygous normal subjects.

Figure 2:
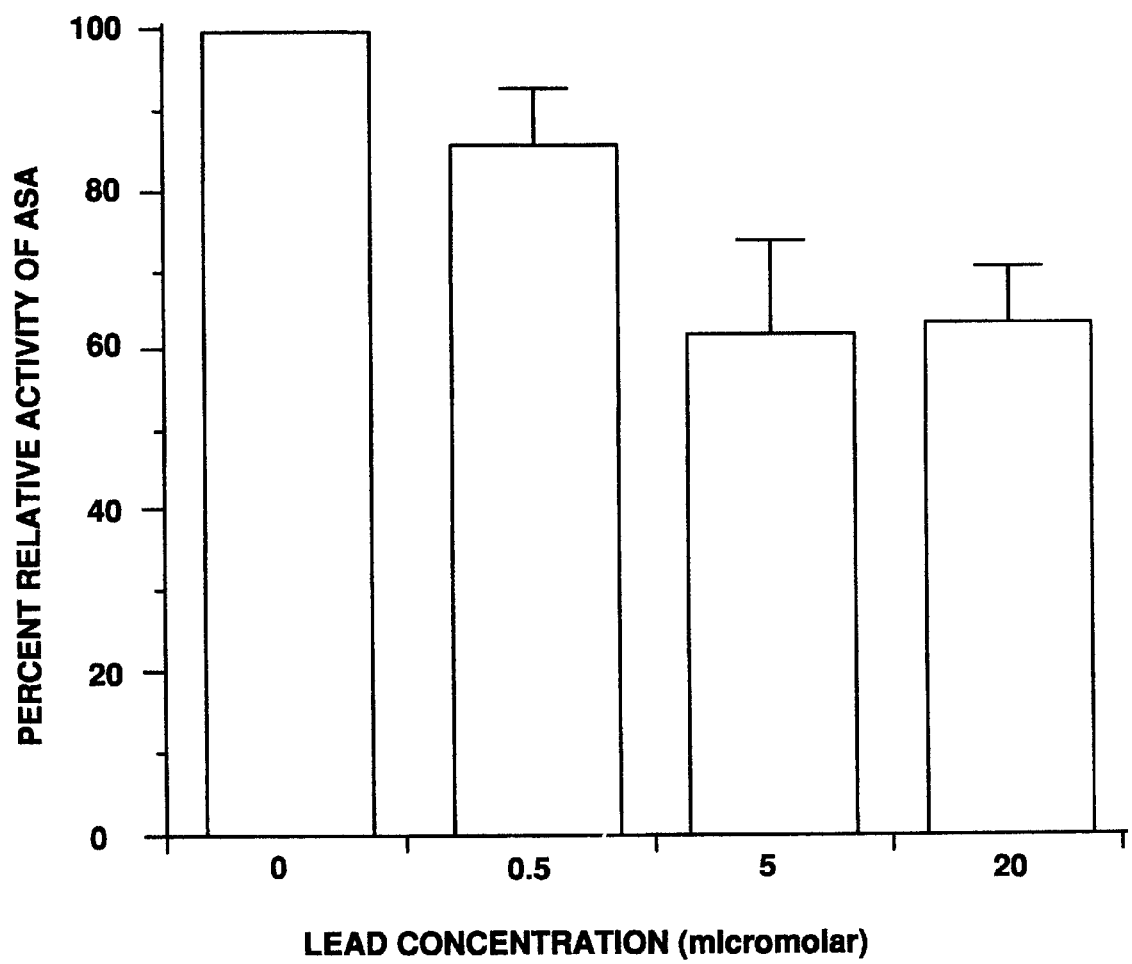
FIG. 2. The effect of lead acetate on intracellular ASA enzymic activity in cultured human fibroblasts. Fibroblasts were grown in vitro as monolayer cultures in the absence or presence of different concentrations of lead acetate as described in the text. The cells were dissolved in buffer containing detergent and the enzymic activity of ASA and other lysosomal enzymes and protein concentration were determined. The data are expressed relative to the control and the s.e.m. at each concentration of lead is indicated.

The potential effect of lead on cellular levels of ASA was examined in an in vitro system employing human fibroblasts. Skin biopsies were obtained from donors who possessed the normal ASA gene (not containing either mutation indicative of PD-ASA) and exhibit normal levels of fibroblast ASA. Fibroblast cultures were derived from punch biopsies and maintained in glutamine/penicillin/streptomycin/fetal bovine serum supplemented EMEM or in the same supplemented medium containing 0.5. 5.0. or 20 μM lead acetate. These cultures were split every three cell cycles for a total of 6–12 cell divisions. Fibroblasts in logarithmic growth were washed with PBS and dissolved in 1 mL of PBS containing 0.1% Triton X-100. This suspension was centriftiged for 5 min at 12,000 ×g and the supernatant was employed for determination of ASA and arylsulfatase B (ASB) activities using p-nitrocatechol sulfate as described by Baum et al. [*Clin. Chim. Acta* 4:453–455 (1959)] and β-galactosidase [Poretz et al., supra]. Each assay was performed in triplicate, and the complete experiment was repeated three times on different occasions for evaluating the effect of lead on cellular levels of ASA. As shown in FIG. 2, lead at concentrations as low as 5 15 μM has a significant effect on cellular specific activity of ASA (units/per mg. of cellular protein) when compared to cells grown in normal medium, as determine by a paired student's t-test (p=0.026). The lead-related reduction of ASA results in up to a 32–36% decrease of this lysosomal enzyme activity when cells are grown in the presence of 20 μM lead (p=0.015). Though the lowest concentration of lead used, 0.5 μM, appears to follow the trend, the 14% reduction is not statistically significant (p=0.260). The lead effect is not limited to ASA but similar reductions were observed for ASB and lysosomal β-galactosidase (data not shown).

In order to determine if the lead-induced rejection of fibroblast ASA enzymic activity is caused by inhibition of the activity, or a decrease in steady-state levels of ASA protein, we performed quantitative PAGE-western immunoblot analysis. Extracts of control cells and cells exposed to lead were analyzed for total protein, and ASA protein. The level of ASA protein was determined using a polyclonal antibody specific for ASA. From the data shown in Table 1, it is evident that lead causes a reduction in steady state levels of specific ASA protein. It is further apparent that the maximum effect of lead occurs during the first ten days of exposure and this effect is sustained for at least 35 days of continuous exposure.

As such, we conclude that exposure of fibroblasts to 20 μM lead causes an approximately 64% reduction in cellular levels of the enzyme protein.

TABLE 1

The Effect of Lead Exposure on Specific Cellular ASA Protein in Human Fibroblasts[1]

| Experiment Number* | Percent ASA Relative to Control Immunoreactive Protein** |
|---|---|
| 1 | 33 |
| 2 | 38 |
| 3 | 38 |

[1]Cells were treated with zero (control) or 20 μM lead acetate and harvested as described for FIG. 2. The extract was partially purified and assayed for total protein as described in Park et al. (Alcoholism: Clin. Exper. Res. 20: 234, 1996). ASA protein was determined by quantitative PAGE-Western immunoblot analysis (Poretz et al., Biochem. J. 287: 979, 1992) utilizing videodensitometry employing the NIH Image program.
*Each experiment represents a different flask of experimental cells. Cells in each experiment were exposed to lead for different lengths of time in terms of cell passages (approximately 5 days/passage). Experiment number 1, exposes to lead for 7 passage; 2, exposed to lead for 3 passages; 3, exposed to lead for 2 passages.
**Denotes the quantity of anti-ASA antibody detectable ASA protein on a Western immunoblot per μg of total cellular protein applied to the sample well, as a percent of that value for the control cells not exposed to lead. The PAGE-Western immunoblot was replicated twice for each experiment and the protein assays were performed in triplicate. The values reported are averages of those obtained for the replicates or triplicates.

Figure 3:
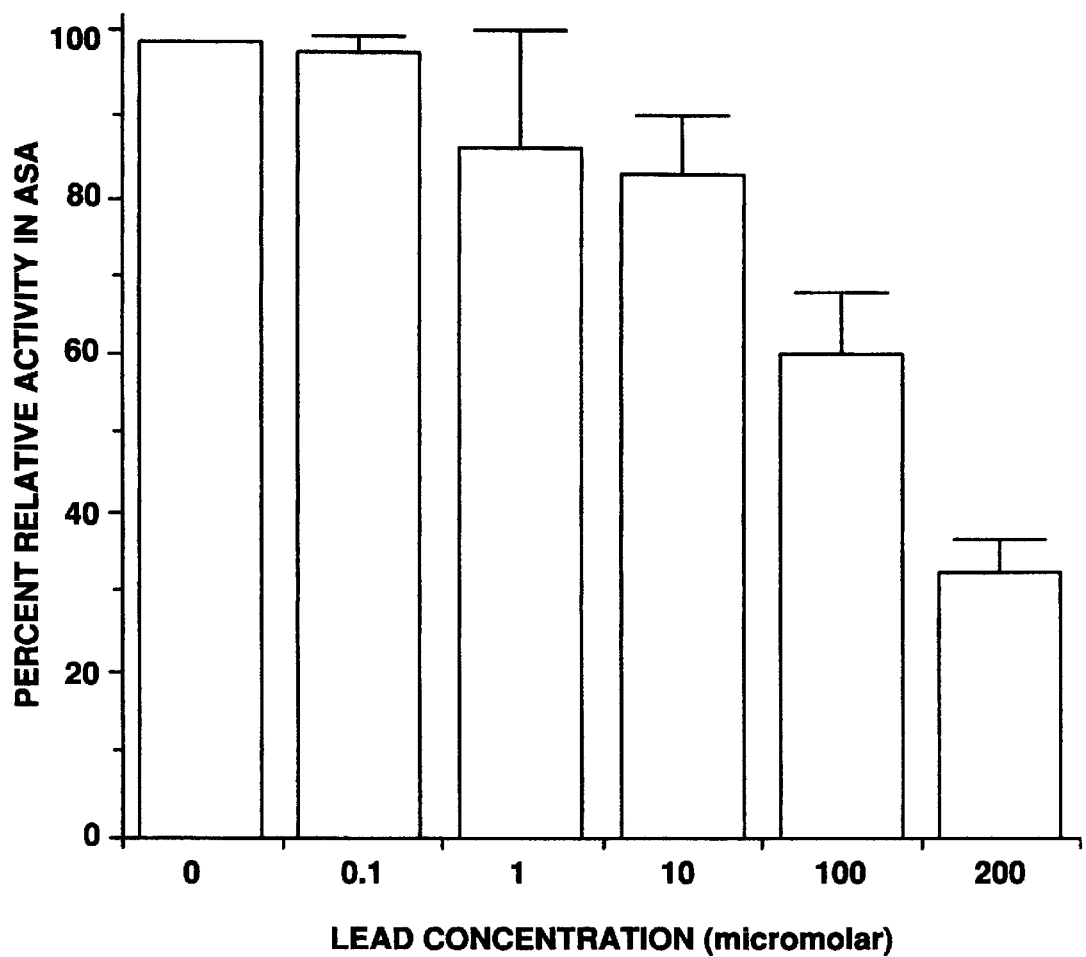
FIG. 3. The effect of lead on the activity of partially purified ASA. A preparation of partially purified human fibroblast ASA containing other lysosomal hydrolases was incubated for 1 hr at 4° C. in the presence of lead acetate as described in the text. ASA and other hydrolase enzymic activities were determined. The data are expressed relative to the control and the s.e.m at each concentration of lead is indicated.

The direct effect of lead on ASA activity was also studied. Relatively high concentrations of lead acetate (100–200 μM) when added to a preparation of partially purified ASA obtained from isolated lysosomes caused precipitation of the enzyme and loss of enzymic activity (see FIG. 3). Human fibroblast ASA was enriched in a preparation of isolated lysosomal enzymes as described by Gorman and Poretz [J. Cell. Physiol. 131:158–164 (1987)]. Lead acetate in buffer was added to protein preparations containing approximately 2 units of ASA activity in a total volume of 2.0 ml and incubated at 4° C. A control lacking lead was also prepared in an identical fashion. Aliquots were removed at 30 min, 1 hr, 24 hr, and 48 hr and analyzed for ASA, β-galactosidase and β-hexosaminidase activities. Enzymic and protein analyses were performed in triplicate, and the complete experiment was repeated three times. The maximum effect was observed at 1 hr. and remained unchanged for up to 48 hr. As shown in FIG. 3, a 67% loss of ASA activity was observed with samples containing 200 μM lead acetate (p=0.045). This effect appeared to exhibit a concentration dependent trend, though the significance of the data below the highest concentration employed was relatively weak (p=0. 129 at 100 μM). Interestingly, the effect of lead acetate on β-hexosaminidase activity closely paralleled that for ASA activity at every concentration of metal studied, but similar conditions caused no reduction of β-galactosidase activity. Apparently, this lead effect does exhibit some specificity.

To more completely understand the potential impact of the PD-ASA polymorphisms on the US population, the ASA genotypes of 86 Americans was determined. Table 2 shows that the gene frequency of the N-glycosylation site mutation for PD-ASA in Caucasian-Americans is 0.22. The associated PD-ASA mutation at the polyadenylation signal sequence is coincident with the N-glycosylation site polymorphism in 47% of these genes. The frequencies are consistent with the results reported by others for the British [Barth et al., J. Med. Genet., 31:667–671 (1994)] and Australian [Nelson et al., supra] populations. In virtually all studies, however, the polyadenylation signal sequence mutation is evident only with the corresponding mutation at the N-glycosylation site sequence.

Only one person has been found in any study to possess the rare condition of the PD-ASA polymorphism at the polyadenylation signal site but not at the N-glycosylation site. Most interesting is the finding that the African-American population has a 1.7-fold greater frequency of the N-glycosylation site mutation than found in the corresponding European derived population. Furthermore, the African-Americans lack the PD-ASA mutation at the polyadenylation signal sequence. The results for the two homogeneous native South African populations shown in Table 2, further substantiate the distinctive pattern of ASA mutations observed for the African-American population. Similar results for the African- and European-Canadian populations were reported recently in abstract form (Ott et al., 1994). From these results it is clear that three times more African-Americans than European-Americans have the homozygous state for the N-glycosylation mutation of PD-ASA.

TABLE 2

Occurrence of ASA Pseudodeficiency Mutations in Different Populations

| Population | No. of Subjects | Frequency of Pseudodeficiency Haplotypes (%)* | | | Frequency of Pseudodeficiency Mutations (%) | |
|---|---|---|---|---|---|---|
| | | 1788G/ 2723A | 1788G/ 2723G** | 1788A/ 2723G | 1788G | 2723G |
| Caucasian-American | 67 | 11.9 | 10.4 | 0.75 | 22.4 | 11.2 |
| African-Americans | 19 | 37 | 0 | 0 | 37 | 0 |
| S. African Bantu | 24 | 44 | 0 | 0 | 44 | 0 |
| S. African San | 23 | 22 | 0 | 0 | 22 | 0 |

*Residue 1788 is at the N-glycosylation site and residue 2723 is at the polyadenylation signal.
**Assumes individuals heterozygous at both pseudodeficiency sites have the A→G transitions at the two pseudodeficiency sites on the same gene.

DISCUSSION

Individuals with Pseudodeficient ASA Possess a Critical Threshold Level of the Enzyme. Intracellular sulfatide metabolism requires proper membrane trafficking and an auxiliary lysosomal protein, saposin B, which facilitates presentation of the glycolipid substrate to ASA [Fürst and Sandhoff, Biochem. Biophys. Acta 1126:1–16 (1992)].

Accordingly, the ability of cells to catabolize sulfatide must be measured in whole cells using the natural substrate. The utilization of a water soluble substrate with cell extracts is a measure of ASA enzymic activity levels only, but is not a correct measure of the ability of the cell to desulfate sulfatide. Fibroblasts from normal subjects, grown in vitro in tissue culture and presented with exogenous sulfatide in the growth medium, are able to incorporate the glycolipid and effect its degradation. This measurement of sulfatide catabolism by cultured cells is called the sulfatide loading test [Kolodny and Fluharty, supra]. As shown in FIG. 1, the sulfatide loading test shows that normal cells contain an apparent 4–5 fold excess of ASA for normal sulfatide metabolism. Thus, decreased ASA levels in homozygous PD-ASA individuals are nevertheless sufficient for normal sulfatide metabolism. Reduction of ASA activity below the level expressed by PD-ASA individuals appears to result in reduced sulfatide catabolism as denoted by the sulfatide loading test. Evidently, the amount of ASA activity in homozygous PD-ASA individuals is at a critical threshold level which still allows normal, or near normal, sulfatide metabolism. These individuals often are not found with symptoms related to MLD. However, no studies have been published to date which present the urinary sulfatide levels of subjects with the PD-ASA genotype. Isolated reports do describe associations of reduced levels of ASA (in the range for PD-ASA) with neurobehavioral conditions, including mental retardation in children [Kihara et al., *Clin. Genet.* 21:253–261 (1982); Sangiorgi et al., *Lancet* 337:802–803 (1991)], abnormal cognitive and emotional responses [Christomanou et al., *Hum. Genet.* 55:103–110 (1980)], and neuropsychiatric symptoms [Propping et al., *Hum. Genet.* 74:244–248 (1986); Shah et al., *Biol. Psychiatr.* 20:50–57 (1985); Heavey et al., *Acta Psychiatr. Scand.* 82:55–59 (1990); Sangiorgi et al., *Amer. J. Med. Genet.* 40:365–369 (1991) and (1991), supra]. N-glycosylation site gene abnormality of PD-ASA associates to a high degree with individuals hospitalized for alcoholism and diagnosed with neuropsychiatric abnormalities.

The concept of a critical threshold level of enzyme was presented by Conzelmann and Sandhoff [*Dev. Neurosci.* 6:58–71 (1983/83)] in their theoretical discussion on the correlation between residual enzyme activities in inherited enzyme deficiencies and the development of neurological disorders. As shown in FIG. 1, they have also confirmed experimentally that below the critical threshold level of ASA, the rate of sulfatide catabolism decreases nearly linearly with residual ASA activity [see Conzelmann and Sandhoff, supra; Leinekugel et al., supra]. It may be expected that exogenous substances which have a negative impact on cellular ASA levels may result in reduced sulfatide catabolism, especially in those individuals who have an hereditary partial deficiency of the enzyme, causing elevated sulfatide levels approaching those observed in mildly affected MLD patients. Given the frequency of the N-glycosylation site polymorphism of PD-ASA (see above), and its consequence on the steady-state levels of cellular ASA, it is evident that 5.0% of the Caucasian population, and three times this frequency of the population of African descendants in the U.S. express the homozygous state of a congenital abnormality which results in reduced, near critical threshold levels of ASA.

Exposure to Lead Causes a Decrease of Cellular ASA in Animals and Cultured Human Cells. The experiments described herein were designed to reveal the role of lead in neurological damage. The working premise is that lead causes reduced levels of ASA in genetically predisposed individuals at critical stages of development of the nervous system. The similarities of the neurobehavioral symptoms of individuals exposed to toxic levels of lead and those who exhibit reduced levels of ASA may be more than coincidental. Evidence accumulated herein supports the contention that lead-induced neurotoxicity is mediated in part, through the impact of the metal on cellular levels of ASA. In whole animal studies, rats fed a basal diet and injected daily with an i.p. dose of lead acetate (100 mg/kg body weight) exhibited a reduction in ASA activity of 55% and 20% in liver and kidney respectively, as compared to control animals [Santra et al., *Ind. J. Biochem. Biophys.* 26:92–97 (1989)]. Evidence from different types of experiments also support the link between lead and ASA. Human fibroblasts possessing the normal gene for ASA. when grown in tissue culture in medium containing concentrations of lead similar to blood lead levels found in affected individuals, contain as little as 65% the amount of ASA expressed by control cells grown in the absence of lead. The lead effect is not limited to ASA but similar reductions were observed for arylsulfatase B and lysosomal γ-galactosidase. Apparently, the impact of lead on fibroblasts affects a number of lysosomal enzymes, perhaps by causing lysosomal instability [Lemons and Thoene, supra; Orsi et al., *Adv. Aerobiol.* 51:243–248 (1987); Brun and Brunk, supra] as well as by altering other factors of cellular homeostasis. Though the concentrations of lead used in these experiments are within the moderate to high range of blood-lead levels found in affected individuals, it must be remembered that fibroblasts are thought to be relatively refractory toward the effects of lead [Tiffany-Castiglioni et al., *Toxicology* 42:303–315 (1986)]. It is reasonable to expect that oligodendrocytes in the developing nervous system of the fetus or young infant may be considerably more sensitive to this lead effect at even lower concentrations of the metal [see Tiffany-Castiglioni et al., supra]. Consistent with the reduction of ASA in cells treated with lead, ASA and other glycolipid hydrolases extracted from human lysosomes, are inactivated when incubated, in vitro, with relatively high concentrations of lead.

ASA possesses two free cysteine residues [Waheed and Van Etten, *Biochim. Biophys. Acta* 831:67–73 (1985)] potentially capable of binding lead. However, the molecular mechanism by which lead causes reduced ASA activity in whole animals or living cells, cultured in vitro, may be more complicated than by the direct interaction of the metal with the enzyme. Of particular interest, Lemons and Thoene [*J. Biol. Chem.* 266:14378–14382 (1991)] reported that facilitated calcium transport by isolated lysosomes is markedly increased by lead at concentrations as low as 300 μM and in a concentration dependent manner. This is in contrast to most other divalent metals tested, which inhibited this process. These authors noted that the consequence of this lead effect is to adversely affect lysosome integrity, causing a greater than 200-fold decrease in the stability of this organelle. A similar effect of lead on the stability of isolated lysosomes also had been published previously [Orsi et al., *Adv. Aerobiol.* 51:243–248 (1987)]. Furthermore, Brun and Brunk [*Acta Pathol. Microbiol. Scand.* 82:311–318 (1974)] reported the histochemical detection of a lead-induced reduction in lysosomal membrane stability in tissue cultured rat fibroblasts exposed to lead nitrate in the growth medium. Presumably, the effect of this lead-induced process in whole cells results in decreased intracellular levels of lysosomal enzymes. Though the possible involvement of calcium-mediated pathways may be critical for the observed effects of lead on cellular ASA levels, the focus of the present Example is the effect of lead on ASA levels and the impact of this on human health.

Recognition of the similarities of the symptoms observed with lead-induced neurotoxicity and those caused by reduced levels of ASA, and the effect of lead on cellular ASA levels and induction of lysosomal instability, individuals who have critical threshold levels of ASA may be hypersusceptible to the neurotoxic effects of the metal, due to lead-related abnormally elevated levels of sulfatide. An inherited hypersusceptibility to lead-induced increases of sulfatide is of special significance with neonates, infants, and young children during periods requiring regulated intracellular sulfatide levels at critical stages of neurodevelopment.

From gene frequency studies, it is clear that the percentage of African-Americans who are homozygous for the N-glycosylation mutation of PD-ASA is three times greater than that percentage detected in the European-American population. Accordingly, a correlate hypothesis is that the African-American population has a three-fold greater risk for being hypersusceptible to lead through the mechanism described than a comparable European-American population. This finding is of even greater significance in light of the results that a greater proportion of the African-American population present with "high" blood-lead levels than seen in the European-American population [see Lin-Fu, supra]. These two factors, one genetic and the other environmental, would place the African-Americans at particular risk for lead-induced neurological deficits.

Chronic, "relatively low" levels of lead exposure especially during the prenatal and early neurodevelopmental formative years, causes cognitive deficits, and abnormal verbal, perceptual and motor function, as measured by a number of criteria and often evidenced as learning and behavioral problems, in affected children. An inherited hypersusceptibility to lead-neurotoxicity is important to define and characterize in order to identify pregnant woman and infants who are at greater risk to the effects of low levels of the metal. A consequence of this research may be the identification of individuals in an at risk population who are hypersusceptible to lead neurotoxicity and therefore may be targeted for treatment, as well as allowing for a more detailed dissection of the biochemical processes involved in lead-induced neuropathologies.

EXAMPLE 2

A Method for Rapid Detection of Arylsulfatase A Pseudodeficiency Mutations

Pseudodeficiency of arylsulfatase A is a complicating factor in the determination of metachromatic leukodystrophy risk and carrier status. A method using PCR and restriction enzyme digestion to detect the presence of both the mutations that contribute to arylsulfatase A pseudodeficiency is described using DNA from blood r buccal cells. Application of this technique should facilitate determination of metachromatic leukodystrophy status and counseling in families where the pseudodeficiency allele is present.

Materials and Methods

DNA isolation. Genomic DNA was isolated from white blood cells by proteinase K digestion and phenol extraction as described (Ausubel et al., 1994, in Current Protocols in Molecular Biology, John Wiley and Sons: New York). Buccal cells were collected on a cytology brush and DNA was prepared by heating in 50 mM sodium hydroxide and neutralization with Tris as described (Richards et al., 1993, Hum. Molec. Genet. 2:159–163).

PCR amplification. Oligonucleotide primers for PCR amplification were designed with the aid of the MacVector program (Eastman Kodak) and obtained from National Biosciences (Plymouth, Minn.). A 200 base pair fragment spanning the third potential N-glycosylation site at amino acid residue 350 (nucleotide 1049) was amplified with the primers ASA2c (5'-TGATGGCGAACTGAGTGACT) (SEQ ID NO:9) and ASA4nc (5'-AAGGATCTGGGATC AGGGGT) (SEQ ID NO:10) using about 0.5 $\mu$g of blood DNA (or 10 $\mu$l of the buccal DNA) in 50 mM KCl, 10 mM Tris (pH 8.3). 1.5 mM $MgCl_2$, 200 $\mu$M each of dATP, dTTP, dCTP and dGTP and 1.25 units of Taq DNA polymerase. Following an initial denaturation at 95° C. for 3 minutes, amplification was carried out for 35 cycles by denaturation at 95° C. for 30 seconds, annealing at 56° C. for I minute and extension at 72° C. for 30 seconds in a 50 $\mu$l volume using an MJ Research PTC100 thermal cycler.

A 182 base pair fragment spanning the polyadenylation signal site at cDNA nucleotide 1620 was amplified with primers ASA3c (5'-AGCTTGCTGCCATTGCCCA) (SEQ. ID. NO:11) and ASA5nc (5'-CATTACCCCAGG ATTGGTCGAA) (SEQ ID NO:12) using the same conditions described above for the ASA2c/ASA4nc primer pair. However, efficient amplification of the 182 base pair fragment with primers ASA3c and ASA5nc was also achieved using a rapid 2-step cycling program (94° C. for 20 seconds, and 56° C. for 30 seconds for 35 cycles).

Restriction endonuclease treatment and gel electrophoresis. The 200 base pair fragment is cleaved by the restriction endonuclease BsrI when the N-glycosylation site is mutated, resulting in two fragments of 112 and 88 base pairs. Following PCR amplification the reaction was sequentially extracted with an equal volume of phenol and chloroform and the DNA was ethanol precipitated in the presence of 0.3 M sodium acetate. Following a 70% ethanol wash, the pellet was dried and dissolved in 20 $\mu$l of 0.1 mM EDTA, 1 mM Tris (pH 8.0). An aliquot (6 $\mu$l) of the DNA was digested in a final volume of 25 $\mu$l with 10 units BsrI in the buffer provided by the supplier (New England Biolabs) at 65° C. for 3 hours.

The 182 base pair fragment spanning the polyadenylation signal site is efficiently cleaved with MaeIII (Boehringer Mannheim) without the need for organic extraction or ethanol precipitation. A volume of 9.8 $\mu$l was digested with 2 units MaeIII in a final volume of 12 $\mu$l at 55° C. for 3 hours. In the absence of a mutation the 182 base pair fragment is cleaved to fragments of 153 and 29 nucleotides. When the polyadenylation signal sequence is mutated, the 153 base pair fragment is further cleaved to 129 and 24 base pair fragments. All PCR and restriction enzyme digestion products were separated by electrophoresis through 7.5% polyacrylamide gels run in TBE buffer (Ausubel et al., supra) and photographed after staining with ethidium bromide.

Results

Analysis of the ASA genotype using DNA isolated from leukocytes of three individuals is presented in FIG. 4A. Subject 'a' is homozygous normal at both the polyadenylation signal site (nucleotide 1620) and the N-glycosylation site (nucleotide 1049). as the 182 base pair PCR product is reduced to 153 base pairs after treatment with MaeIII, and the 200 base pair fragment spanning the N-glycosylation site is unaffected by treatment with the BsrI. Subject 'b' is homozygous for the presence of the pseudodeficiency mutations at both the polyadenylation signal and N-glycosylation sites, as the 182 base pair product is cleaved to 129 base pairs by MaeIII and the 200 base pair product spanning the mutated N-glycosylation site is completely cleaved to bands of 112 and 88 base pairs by BsrI. Subject 'c' is heterozygous for both sites, having two bands visible in the MaeIII digest (153 and 129 base pairs) and three bands visible in the BsrI digest (200, 112 and 88 base pairs).

FIG. 4B shows an analysis of the ASA genotype using buccal cells from three other individuals as a source of DNA. Subject 'd' is homozygous normal at both sites, subject 'e' heterozygous at both sites and subject 'f' is heterozygous at only the N-glycosylation site. Being able to genotype ASA with DNA from buccal cells means that the sample for analysis can be provided by the subject without discomfort or the need for a phlebotomist, and the entire process of obtaining the sample, DNA isolation, PCR amplification, restriction enzyme digestion and analysis of results can easily be completed in a single day. The genotypes of the subjects analyzed in FIGS. 4A and 4B are summarized in FIG. 4C.

Discussion

In the diagnosis of susceptibility to neurotoxicity and of MLD, and assessment of risk for potential siblings or offspring of individuals carrying these traits, it is important to be able to detect both the pseudodeficiency mutations of ASA in family members of affected persons (Shen et al., supra]. The method presented in this Example is rapid and provides direct visualization of the ASA genotype at both the pseudodeficiency sites. This is particularly important as the N-glycosylation site mutation can occur in the absence of the polyadenylation signal site mutation [Nelson et al., supra: Hohenschutz et al., *Hum. Genet.*, 82:45–48 (1989)], and the N-glycosylation site mutation does appear to influence the enzyme activity [Shen et al., supra; Park et al., *Alcohol. Clin. Exper. Res.* 20:228–233 (1996)]. Furthermore, in some populations the polyadenylation signal site mutation is not found while the N-glycosylation site mutation is encountered at relatively high gene frequencies (Table 2).

An alternative method that has been used for the detection of the pseudodeficiency mutations of ASA include immobilization of PCR products on a membrane and sequential hybridization to the products with allele specific radiolabelled oligonucleotide probes [Gieselmann et al., supra (1989)]. This approach is suited to analysis of very large numbers of samples, but is both expensive and time consuming when applied to smaller numbers of individuals, as is typical in family diagnostic studies.

Two methods to determine the presence of polyadenylation signal site of ASA at nucleotide 1620 of the cDNA, but not the nucleotide 1049 mutation, have also been described [Gieselmann et al., supra (1991); Chabas et al., *Clin. Genet.* 44:320–323 (1993)]. One is an allele-specific amplification assay requiring the use of three pairs of primers for each analysis [Gieselmann et al., supra (1991)], and the second uses a mismatched primer to produce a RsaI restriction site when the polyadenylation signal mutation is present [Chabas et al., supra]. This latter report has overlooked the MaeIII restriction site produced by the polyadenylation signal site mutation.

In summary the methodology described in this Example enables the rapid and accurate detection of the status of both sites known to contribute to pseudodeficiency of ASA in DNA of individuals. This should facilitate the identification and distinction of MLD and ASA pseudodeficiency alleles in family studies, which is important in order to provide genetic counseling to such families in connection with both susceptibility to neurotoxicity and the possibility of developing MLD. Furthermore, the techniques described are applicable to larger investigations designed to determine the relative frequency of the pseudodeficiency mutations in different populations.

EXAMPLE 3

AN IMMUNOASSAY FOR PSEUDODEFICIENT ASA

The immunoassay is an enzyme-linked assay to detect the aberrant enzyme in cellular extracts and/or body fluids of individuals. The basis of the assay is to employ an antibody which can react with ASA lacking the glycan at residue 350 and binds with specificity to only ASA possessing this structural abnormality. The reagent is prepared as a monoclonal antibody elicited to a synthetic antigen possessing the oligopeptide structure analogous to the amino acid sequence surrounding residue 350 of ASA containing a serine residue rather than the normal asparagine residue at this location. Hybridomas secreting such an antibody are identified in screening assays by detecting those which exhibit reactivity toward the mutant ASA but lack reactivity towards the normal enzyme.

An oligopeptide, Ac-CAPLPSVTLDGFD-NH$_2$ (SEQ ID NO:13) has been prepared synthetically (Chiron Mimotopes, San Diego, Calif.). This peptide is covalently coupled via the —SH group of the amino terminal cysteine to diphtheria toxoid and to bovine serum albumin. The serine residue underlined is the amino acid which differs from the asparagine 350 of normal ASA.

Immunization of mice and hybridoma preparation is performed by conventional methods employing the oligopeptide-diphtheria toxoid conjugate and the immunogen (see E. Harlow and D. Lane, in *Antibodies: A Laboratory Manual*, Cold Spring Harbor Laboratory Press: Cold Spring Harbor, N.Y.).

An antigen capture ELISA assay is employed essentially as described by Harlow and Lane, supra. The detection antigens employed are pseudodeficient ASA (prepared as a partially purified extract from fibroblasts of an individual who is homozygous for the mutant enzyme) or normal ASA (prepared as a partially purified extract from fibroblasts of an individual who is homozygous for the normal enzyme). The presence of bound enzyme in the ELISA is detected employing a calorimetric assay for ASA utilizing p-nitrocatachol sulfate by a method similar to that described by Manowitz et al. [*Biol. Psychiat.* 16:1107–1113 (1981)]. Alternatively, hybridomas secreting antibody which reacts with the antigenic oligopeptide are detected by an antibody capture ELISA utilizing the oligopeptide conjugated to bovine serum albumin similar to the procedure described by Harlow and Lane, supra. Positive hybridomas identified in this assay are then screened by the antigen capture assay with mutant and normal ASA as described above. Hybridomas which exhibit reactivity with the mutant enzyme but not the normal enzyme are expanded in either tissue culture (see Harlow and Lane) or in vivo (in ascites) as described by Lee and Poretz [*Immunol. Cell Biol.* 69:151–157 (1991)].

EXAMPLE 4

ENDONUCLEASE DETECTION OF ARYLSULFATASE A PSEUDODEFICIENCY MUTATIONS WITH AN INTERNAL CONTROL

A method of using PCR and restriction enzyme digestion to detect the presence of both mutations that contribute to arylsulfatase A pseudodeficiency is described using DNA from blood or buccal cells. This method employs internal controls for the enzyme activity of both endonucleases.

This Example further describes a method for detecting the presence of both mutations that contribute to arylsulfatase A pseudodeficiency by using PCR and restriction endonuclease digestion of the gene. The primer of the present invention generates a new BsrI site within the PCR product, which is common to both the normal and Pd ASA PCR fragments. Since the Pd sequence, but not the normal, exhibits a second BsrI site, an internal control for restriction enzyme activity is created and allows for a more accurate detection of pseudodeficiency and MLD.

Materials and Methods

DNA isolation. Genomic DNA was isolated from white blood cells, and buccal cells were collected, as described in Example 2, supra.

PCR amplification. Oligonucleotide primers for PCR amplification were designed with the aid of the MacVector program (Eastman Kodak) and obtained from National Biosciences (Plymouth, Minn.). A 211 base pair fragment spanning the third potential N-glycosylation site at amino acid residue 350 (nucleotide 1049) was amplified with the primers ASA17c (5'-CACCCCAACCTTGATG GCGAACTGGGTGAC) (SEQ ID NO:14) and ASA4nc (5'-AAGGATCTGGGATCAGGGGT) (SEQ ID NO:10) using about 0.5 µg of blood DNA (or 10 µl of the buccal DNA preparation) in 50 mM KCl, 10 mM Tris (pH 8.3), 1.5 mM MgCl$_2$, 200 µM each of dATP, dTTP, dCTP and dGTP and 1.25 units of Taq DNA polymerase. Following an initial denaturation at 95° C. for 3 minutes, amplification was carried out for 35 cycles by denaturation at 95° C. for 30 seconds, annealing at 56° C. for 1 minute and extension at 72° C. for 30 seconds in a 50 µl volume using an MJ Research PTC100 thermal cycler. The oligonucleotide primer ASA17c has a single nucleotide mismatch 6 nucleotides from the 3' terminus (bold). This introduces a BsrI restriction endonuclease recognition sequence (ACTGGN) twenty-five nucleotides from the endo of the amplified product.

A 182 base pair fragment spanning the polyadenylation signal site at cDNA nucleotide 1620 was amplified with primers ASA3c (5'-AGCTTGCTGCCATTGCCCA) (SEQ ID NO:11) and ASA5nc (5'-CATTACCCCAGG ATTGGTCGAA) (SEQ ID NO:12) using the same conditions described above for the ASA2c/ASA4nc primer pair. However, efficient amplification of the 182 base pair fragment with primers ASA3c and ASA5nc was also achieved using a rapid 2-step cycling program (94° C. for 20 seconds, and 56° C. for 30 seconds for 35 cycles).

Restriction endonuclease treatment and gel electrophoresis. The 211 base pair fragment is cleaved by the restriction endonuclease BsrI at the engineered site within the primer ASA17c to produce fragments of 186 and 25 base pairs when the N-glycosylation coding site is not mutated. This serves as an internal positive control for BsrI activity. When the N-glycosylation site coding site at nucleotide 1049 is mutated, the 186 base pair fragment is further cut to fragments of 98 and 88 base pairs. Following PCR amplification the reaction was sequentially extracted with an equal volume of phenol and chloroform and the DNA was ethanol precipitated in the presence of 0.3 M sodium acetate. Following a 70% ethanol wash, the pellet was dried and dissolved in 20 µl of 0.1 mM EDTA, 1 mM Tris (pH 8.0). An aliquot (6 µl) of the DNA was digested in a final volume of 25 µl with 10 units BsrI in the buffer provided by the supplier (New England Biolabs) at 65° C. for 3 hours.

Cleavage conditions with for the 182 base pair fragment spanning the polyadenylation signal site are described in Example 2, supra.

Results

The oligonucleotide primer pairs for this Example were designed to amplify genomic DNA fragments spanning each of the two pseudodeficiency mutation sites and to include internal positive controls for endonuclease activity. Thus, in addition to the potential BsrI site at nucleotide 1049 in the mutant ASA gene, the 211 base pair product spanning this region has an engineered BsrI site 25 nucleotides from the 5' end. Similarly, the 182 nucleotide product spanning the polyadenylation signal site has, in addition to the potential MaeIII site at nucleotide 1620, a naturally occurring MaeIII site 29 nucleotides from the 3' end of the PCR product. These constant cutting sites serve as internal controls of the restriction enzyme activity.

Analysis of the ASA genotype using DNA isolated from leukocytes of three individuals is presented in FIGS. 5A and 5B. FIG. 5A shows the PCR amplified product spanning the N-glycosylation site without enzyme digestion(-) or after digestion with BsrI in subjects a, b, and c. The 211 base pair band is cleaved into 186 base pairs in the absence of the N-glycosylation site mutation (as for subject c), and to fragments of 98 and 88 base pairs in the subject homozygous for the mutation at this position (b). Subject a has bands of 186, 98, and 88 base pairs, and is therefore heterozygous for the N-glycosylation site mutation.

Similarly, the genotype at the polyadenylation signal site can be easily detected by digestion of the 182 base pair PCR product with MaeIII. This produces a band of 153 base pairs in the absence of the mutation and 129 base pairs when the mutation is present. Subject a has both the 153 and 129 base pair bands after MaeIII digestion (FIG. 5B), and is therefore heterozygous for the polyadenylation signal site pseudodeficiency mutation.

Note that the smaller products of the restriction enzyme digestions are less than 30 base pairs in size and cannot be seen on the gels.

A crude DNA preparation can be rapidly prepared from buccal epithelial cells obtained in a non-invasive manner with a cytology brush [Richards et al., Hum. Mol. Genet. 2:159–163 (1993)]. FIGS. 5C and 5D show that such DNA can be efficiently amplified and analyzed using the PCR-restriction enzyme assay described in this paper. The ASA genotypes of the five subjects analyzed are summarized in FIG. 5E. The platelet ASA activity of subjects a and b were 75% and 14.5% of normal, respectively.

Discussion

As noted above, in the diagnosis of susceptibility to neurotoxicity, as well as MLD and assessment of risk for potential siblings, it is important to be able to accurately detect both the pseudodeficiency mutations of ASA in family members of affected persons. The method presented in this Example is rapid and provides direct visualization of the ASA genotype at both ASA pseudodeficiency sites. Moreover, use of a PCR primer with a single mismatch (ASA17c) to create a control BsrI site provides a positive control for the restriction enzyme activity. It was found that a 10 nucleotide shorter oligonucleotide primer with the same mismatch did not cut with BsrI, indicating that this restriction enzyme requires more than 10 nucleotides flanking its recognition site in order to efficiently cleave the DNA.

In summary, the methodology described herein enables the rapid and accurate detection of the status of both sites known to contribute to pseudodeficiency of ASA in DNA of individuals, with internal positive controls for endonuclease activity for both sites. This should facilitate the identification and distinction of MLD and ASA pseudodeficiency alleles in family studies, which is important in order to provide genetic counseling to such families.

The foregoing examples have been provided for a better understanding of the invention and as an illustrative description presenting the details of the constructs and procedures that were followed in its development and validation. The invention is not intended to be limited to the examples. This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein. It is also to be understood that all base pair sizes given for nucleotides and all molecular weight information for proteins are approximate and are used for the purpose of description. Various references are cited throughout this specification, each of which is incorporated herein by reference in its entirety.

What is claimed is:

1. A method for identifying an individual who may be susceptible to neurotoxicity or to the pathological effects of toxicants comprising identifying whether an individual is homozygous, heterozygous, or normal for a pseudodeficiency (PD) mutation of the arylsulfatase A (ASA) gene, wherein heterozygosity for a PD mutation indicates that the individual may be susceptible to neurotoxicity or the pathological effects of toxicants, and homozygosity for the PD mutation of the ASA gene indicates that the individual may be more susceptible to neurotoxicity or to the pathological effects of toxicants than the heterozygous PD/normal individual.

2. The method according to claim 1, wherein the method of identifying an individual who is heterozygous or homozygous for a PD mutation comprises detect a mutation in a residue 350 N-glycosylation site of ASA.

3. The method according to claim 1, wherein the method of identifying an individual who is heterozygous homozygous for a PD mutation comprises detecting a mutation in a polyadenylation signal sequence of at least one allele of ASA.

4. The method according to claim 1, wherein the method of identifying an individual who is heterozygous or homozygous for a PD mutation comprises detecting a mutation in the residue 350 N-glycosylation site of ASA and detecting a mutation in the polyadenylation signal sequence of the allele of ASA.

5. The method according to claim 2, wherein the mutation in the N-glycosylation site is detected by polymerase chain amplification (PCR) analysis.

6. The method according to claim 5, wherein the PCR product of the mutant and normal N-glycosylation in site can be differentiated by specific restriction endonucleases.

7. The method according to claim 6, wherein the PCR analysis is performed by:
   a) amplifying an approximately 211-base pair segment of genomic DNA with a 5' primer CACCCCAACCT-TGATGGCGAACTGGGTGAC (SEQ ID NO:14), which is engineered to introduce a control BsrI restriction endonuclease site, and a 3' primer AAG-GATCTGGGATCAGGGGT (SEQ ID NO:10); and
   b) detecting the presence of a BsrI restriction endonuclease site in addition to the control BsrI restriction endonuclease site;
   wherein the BsrI endonuclease site is present in the PD mutant ASA allele.

8. The method according to claim 6, wherein the PCR analysis is performed by:
   a) amplifying an approximately 200-base pair segment of genomic DNA with a 5' primer TGATGGCGAACT-GAGTGACT (SEQ ID NO:9) and a 3' primer AAG-GATCTGGGATCAGGGGT (SEQ ID NO:10); and
   b) detecting the presence of a BsrI restriction endonuclease site;
   wherein the BsrI endonuclease site is present in the PD mutant ASA allele.

9. The method according to claim 5, wherein the PCR analysis is performed by amplifying a segment of genomic DNA containing the N-glycosylation site, and detecting hybridization of an oligonucleotide probe selected from the group consisting of AAGGTGACATTGGGCAGTGG (SEQ ID NO:5) and AAGGTGACACTGGGCAGTGG (SEQ ID NO:6) to the amplified sequence, wherein hybridization of the former probe at 55° C. with washing at 62° C. is indicative of a normal ASA allele, and hybridization of the latter probe at 55° C. with washing at 60° C. is indicative of a PD allele.

10. The method according to claim 5, wherein the PCR analysis is performed on DNA obtained from buccal cells.

11. The method according to claim 5, wherein the mutation comprises substitution of guanine for adenine at nucleotide position 1049 of cDNA for ASA.

12. The method according to claim 2, wherein the mutation in the N-glycosylation site is detected by biochemical analysis.

13. The method according to claim 12, wherein the biochemical analysis comprises detecting a difference in the relative electrophoretic mobility of an ASA protein from an individual possessing the mutant ASA enzyme as compared to a norm ASA protein.

14. The method according to claim 2, wherein the mutation in the N-glycosylation site is detected by immunochemical analysis.

15. The method according to claim 14, wherein the immunochemical analysis comprises detecting binding of an antibody specific for an epitope of ASA lacking an N-glycosylation site, wherein the antibody does not bind to normal ASA.

16. The method according to claim 15, wherein the antibody is a monoclonal antibody.

17. The method according to claim 15, wherein the antibody is generated against the peptide Ac-CAPLPSVTLDGFD-NH$_2$ (SEQ ID NO:13).

18. The method according to claim 3, wherein the mutation in the polyadenylation signal sequence is detected by polymerase chain amplification (PCR) analysis.

19. The method according to claim 18, wherein the PCR product of the mutant and normal polyadenylation signal sequence site can be differentiated by specific restriction endonucleases.

20. The method according to claim 19, wherein the PCR analysis is performed by:

a) amplifying about an approximately 182-base pair segment of genomic DNA with a 5' primer AGCTTGCTGCCATTGCCCA (SEQ ID NO:11) and a 3' primer CATTACCCCAGGATTGGTCGAA (SEQ ID NO:12); and b) detecting the presence of two MaeIII restriction endonuclease sites;

wherein two MaeIII endonuclease sites are present in the PD mutant ASA allele.

21. The method according to claim 19, wherein the PCR analysis is performed by amplifying a segment of genomic DNA containing the polyadenylation signal site, and detecting hybridization of an oligonucleotide probe selected from the group consisting of CTGGTGTTATTACGTTATC (SEQ ID NO:7) and CTGGTGTTACTACGTTATC (SEQ ID NO:8) to the amplified sequence, wherein hybridization of the former probe at 48° C. with washing at 52° C. is indicative of a normal ASA allele, and hybridization of the latter probe at 48° C. with washing at 52° C. is indicative of a PD allele.

22. The method according to claim 19, wherein the PCR analysis is performed on DNA obtained from buccal cells.

23. The method according to claim 19, wherein the mutation comprises substitution of guanine for adenine at nucleotide position 1620 of cDNA for ASA.

24. The method according to claim 1, wherein the toxicant is a lysosomotropic drug.

25. The method according to claim 1, wherein the toxicant is a tricyclic antidepressant.

26. The method according to claim 1, wherein the toxicant is lead.

* * * * *

```
                    SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 20 base
pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc
= "PRIMER"

(iii) HYPOTHETICAL: NO (xi) SEQUENCE DESCRIPTION: SEQ ID NO:1:

TGATGGCGAA CTGAGTGACT

20

(2) INFORMATION FOR SEQ ID NO:2:

(i) SEQUENCE CHARACTERISTICS:
         (A) LENGTH: 20 base
pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc
= "PRIMER"

(iii) HYPOTHETICAL: NO (xi) SEQUENCE DESCRIPTION: SEQ ID NO:2:

AAGGATCTGG GATCAGGGGT

20

(2) INFORMATION FOR SEQ ID NO:3:

(i) SEQUENCE CHARACTERISTICS:
         (A) LENGTH: 19 base
pairs
         (B) TYPE: nucleic acid
```

(C) STRANDEDNESS: single
            (D) TOPOLOGY: linear (ii) MOLECULE TYPE: other nucleic acid
            (A) DESCRIPTION: /desc
= "PRIMER"

(iii) HYPOTHETICAL: NO (xi) SEQUENCE DESCRIPTION: SEQ ID NO:3:

AGCTTGCTGC CATTGCCCA

19

(2) INFORMATION FOR SEQ ID NO:4:

(i) SEQUENCE CHARACTERISTICS:
            (A) LENGTH: 22 base
pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc
= "PRIMER"

(iii) HYPOTHETICAL: NO (xi) SEQUENCE DESCRIPTION: SEQ ID NO:4:

CATTACCCCA GGATTGGTCG AA

22

(2) INFORMATION FOR SEQ ID NO:5:

(i) SEQUENCE CHARACTERISTICS:
            (A) LENGTH: 20 base
pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc
= "PRIMER"

(iii) HYPOTHETICAL: NO (xi) SEQUENCE DESCRIPTION: SEQ ID NO:5:

AAGGTGACAT TGGGCAGTGG

20

(2) INFORMATION FOR SEQ ID NO:6:

(i) SEQUENCE CHARACTERISTICS:
            (A) LENGTH: 20 base
pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc
= "PRIMER"

(iii) HYPOTHETICAL: NO (xi) SEQUENCE DESCRIPTION: SEQ ID NO:6:

AAGGTGACAC TGGGCAGTGG

20

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:7:

CTGGTGTTAT TACGTTATC

19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:8:

CTGGTGTTAC TACGTTATC

19

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:9:

TGATGGCGAA CTGAGTGACT

20

(2) INFORMATION FOR SEQ ID NO:10:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: other nucleic acid
        (A) DESCRIPTION: /desc
= "PRIMER"

(iii) HYPOTHETICAL: NO (xi) SEQUENCE DESCRIPTION: SEQ ID NO:10:

AAGGATCTGG GATCAGGGGT

20

(2) INFORMATION FOR SEQ ID NO:11:

(i) SEQUENCE CHARACTERISTICS:
        (A) LENGTH: 19 base
pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc
= "PRIMER"

(iii) HYPOTHETICAL: NO (xi) SEQUENCE DESCRIPTION: SEQ ID NO:11:

AGCTTGCTGC CATTGCCCA

19

(2) INFORMATION FOR SEQ ID NO:12:

(i) SEQUENCE CHARACTERISTICS:
        (A) LENGTH: 22 base
pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc
= "PRIMER"

(iii) HYPOTHETICAL: NO (xi) SEQUENCE DESCRIPTION: SEQ ID NO:12:

CATTACCCCA GGATTGGTCG AA

22

(2) INFORMATION FOR SEQ ID NO:13:

(i) SEQUENCE CHARACTERISTICS:
        (A) LENGTH: 13 amino
acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:13:

Asp Phe Gly Asp Leu Thr Val Ser Pro Leu Pr
o Ala Cys
1                   5

-continued

```
(2) INFORMATION FOR SEQ ID NO:14:

(i) SEQUENCE CHARACTERISTICS:
        (A) LENGTH: 30 base
pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc
= "PRIMER"

(iii) HYPOTHETICAL: NO (xi) SEQUENCE DESCRIPTION: SEQ ID NO:14:

CACCCCAACC TTGATGGCGA ACTGGGTGAC
            30
```